US012639965B2

(12) United States Patent
Ravishankar et al.

(10) Patent No.: US 12,639,965 B2
(45) Date of Patent: May 26, 2026

(54) ITERATIVE FRAMEWORK FOR LEARNING MULTIMODAL MAPPINGS TAILORED TO MEDICAL IMAGE INFERENCING TASKS

(71) Applicant: GE Precision Healthcare LLC, Waukesha, WI (US)

(72) Inventors: Hariharan Ravishankar, Bengaluru (IN); Vikram Reddy Melapudi, Bangalore (IN); Pavan Annangi, Bangalore (IN); Abhijit Patil, Bengaluru (IN)

(73) Assignee: GE Precision Healthcare LLC, Waukesha, WI (US)

( * ) Notice: Subject to any disclaimer, the term of this patent is extended or adjusted under 35 U.S.C. 154(b) by 277 days.

(21) Appl. No.: 18/471,836

(22) Filed: Sep. 21, 2023

(65) Prior Publication Data

US 2025/0104451 A1 Mar. 27, 2025

(51) Int. Cl.

| | |
|---|---|
| ***G06V 20/70*** | (2022.01) |
| ***G06N 5/04*** | (2023.01) |
| ***G06V 10/774*** | (2022.01) |
| ***G06V 10/776*** | (2022.01) |

(Continued)

(52) U.S. Cl.
CPC ............... *G06V 20/70* (2022.01); *G06N 5/04* (2013.01); *G06V 10/774* (2022.01); *G06V 10/776* (2022.01); *G16H 30/40* (2018.01); *G06V 2201/03* (2022.01); *G16H 10/60* (2018.01)

(58) Field of Classification Search
CPC .................................................... G06V 10/764
See application file for complete search history.

(56) References Cited

U.S. PATENT DOCUMENTS 11,030,763 B1 * 6/2021 Srivastava .............. G06T 7/593
12,367,261 B1 * 7/2025 Tam ..................... G06V 10/774

(Continued)

OTHER PUBLICATIONS

Bommasani, R. et al. | "On the opportunities and risks of foundation models." arXiv preprint arXiv:2108.07258v3 [cs.LG] Jul. 12, 2022, 214 pages.

(Continued)

*Primary Examiner* — Di Xiao
(74) *Attorney, Agent, or Firm* — Amin, Turocy & Watson, LLP

(57) ABSTRACT

An iterative framework for learning multimodal mappings tailored to medical image inferencing tasks is provided. In an example, a computer-implemented method can comprise receiving multimodal annotation data for medical images, the multimodal annotation data comprising non-image annotation data and image annotation data, and employing one or more machine learning (ML) processes to learn bi-directional mappings between non-image features included in the non-image annotation data and image features associated with the medical images and the image annotation data. The method further comprises generating, as a result of the one or more ML processes, a model configured to: infer one or more of the non-image features associated with new medical images given the new medical images, and/or infer one or more of the image features associated with the new medical images given the new medical images and non-image input corresponding to at least some of the non-image annotation data.

20 Claims, 10 Drawing Sheets

(51) Int. Cl.
*G16H 30/40* (2018.01)
*G16H 10/60* (2018.01)

(56) References Cited

U.S. PATENT DOCUMENTS

| | | | | |
|---|---|---|---|---|
| 2022/0037018 | A1* | 2/2022 | Goede | G06F 18/251 |
| 2023/0351149 | A1* | 11/2023 | Yu | G06N 3/045 |

OTHER PUBLICATIONS

Kirillov, A. et al. | "Segment Anything." arXiv:2304.02643v1 [cs.CV] Apr. 5, 2023, 30 pages.

Luddecke, T. et al. | "Image Segmentation Using Text and Image Prompts." CVPR 2022, arXiv reprint arXiv:2112.10003v2 [cs.CV] Mar. 30, 2022, 14 pages.

* cited by examiner

700

Receiving, by a system comprising a processor, receives multimodal annotation data for medical images included a medical image dataset, the multimodal annotation data comprising non-image annotation data and image annotation data — 702

Employing, by the system, one or more machine learning processes to learn bi-directional mappings between non-image features included in the non-image annotation data and image features associated with the medical images and the image annotation data — 704

Generating, by the system as a result of the one or more machine learning processes, a model configured to infer one or more of the non-image features associated with new medical images given the new medical images — 706

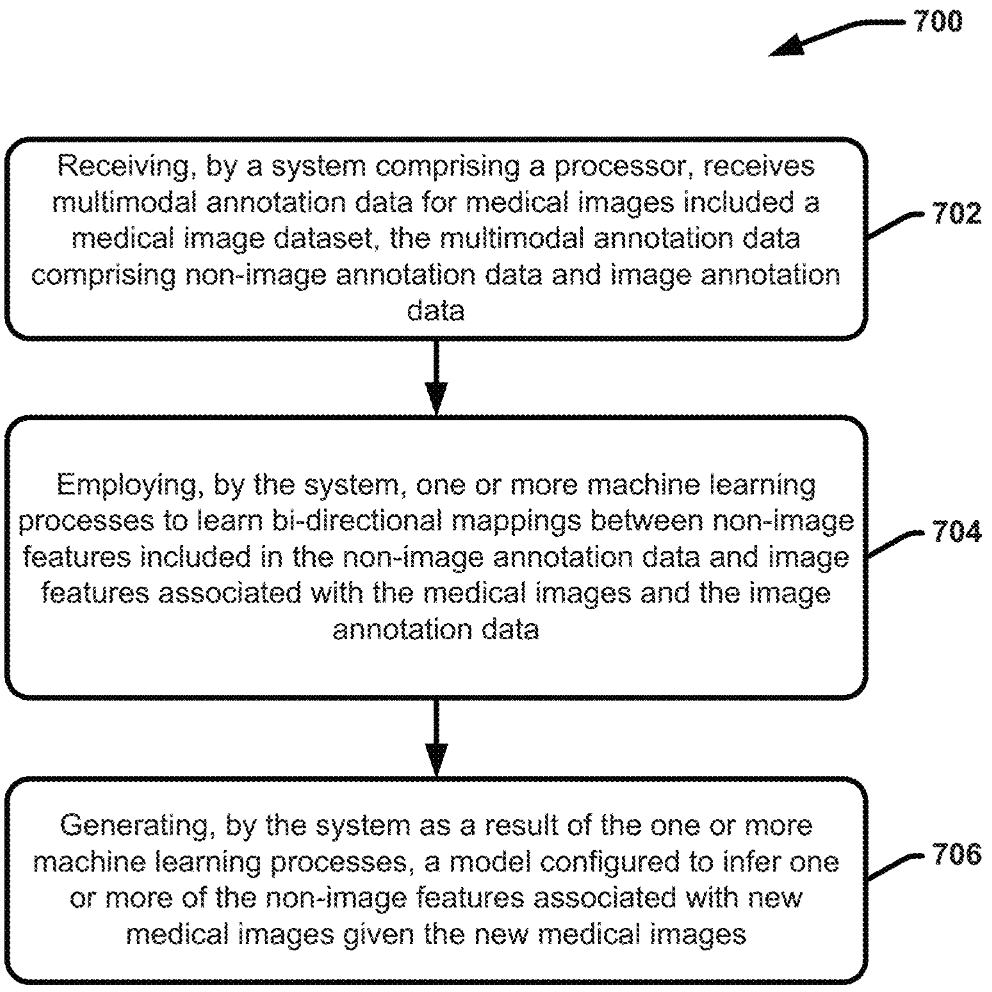

Receiving, by a system comprising a processor, receives multimodal annotation data for medical images included a medical image dataset, the multimodal annotation data comprising non-image annotation data and image annotation data

802

Employing, by the system, one or more machine learning processes to learn bi-directional mappings between non-image features included in the non-image annotation data and image features associated with the medical images and the image annotation data

804

Generating, by the system as a result of the one or more machine learning processes, a model configured to infer one or more of the image features associated with new medical images given the new medical images and non-image input identifying or indicating one or more of the non-image features respectively associated with the new medical images

806

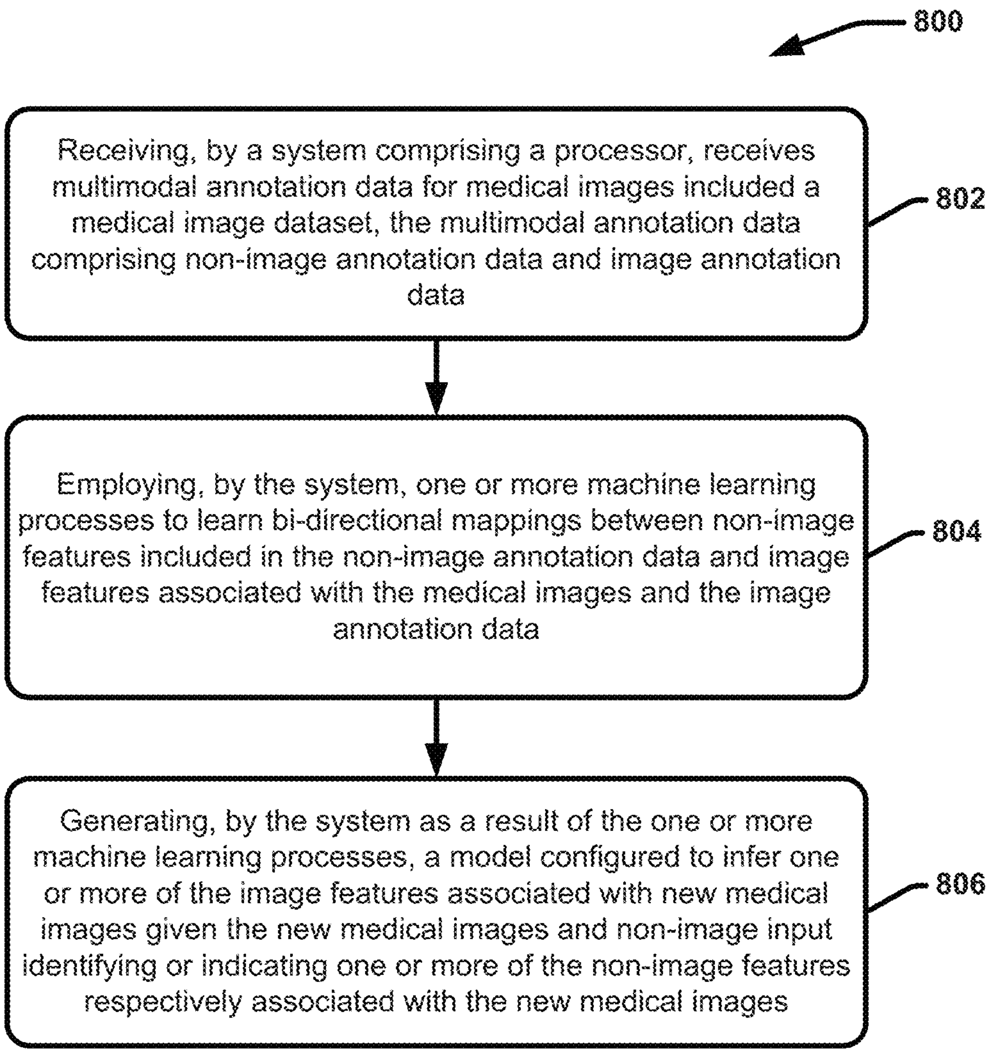

FIG. 8

ITERATIVE FRAMEWORK FOR LEARNING MULTIMODAL MAPPINGS TAILORED TO MEDICAL IMAGE INFERENCING TASKS

TECHNICAL FIELD

This application relates to artificial intelligence (AI) in the medical imaging domain, and more particularly to an iterative framework for learning multimodal mappings tailored to medical image inferencing tasks.

BACKGROUND

Deep learning (DL) models have demonstrated state-of-the-art performance in various medical image processing tasks like organ segmentation, anomaly detection, diagnosis classification, risk prediction, temporal analysis, image reconstruction, and others. However, they suffer from three major issues: 1) requirement of large-scale annotated data, 2) asynchronous model development between different development phases (e.g., data curation and annotation, model building, and report generation, 3) and lack of explainability.

SUMMARY

The following presents a summary to provide a basic understanding of one or more embodiments of the invention. This summary is not intended to identify key or critical elements or delineate any scope of the different embodiments or any scope of the claims. Its sole purpose is to present concepts in a simplified form as a prelude to the more detailed description that is presented later. In one or more embodiments, systems, computer-implemented methods, apparatus and/or computer program products are described that provide an iterative framework for learning multimodal mappings tailored to medical image inferencing tasks.

According to an embodiment, a system is provided that comprises a memory that stores computer-executable components, and a processor that executes the computer-executable components stored in the memory. The computer-executable components can comprise a reception component that receives multimodal annotation data for medical images included a medical image dataset, the multimodal annotation data comprising non-image annotation data (e.g., text data and/or other forms of non-image input) and image annotation data (e.g., mark-up data applied to the medical images). The computer-executable components further comprise a machine learning component that employs one or more machine learning processes to learn bi-directional mappings between non-image features included in the non-image annotation data and image features associated with the medical images and the image annotation data.

In some embodiments, as a result of the one or more machine learning processes, the machine learning component generates a model configured to infer one or more of the non-image features associated with new medical images given the new medical images.

Additionally, or alternatively, as a result of the one or more machine learning processes, the machine learning component generates a model configured to infer one or more of the image features associated with new medical images given the new medical images and non-image input identifying or indicating one or more of the non-image features respectively associated with the new medical images. With these embodiments, in association with inferring the one or more of the image features, the machine learning component can configure the model to generate new image annotation data for the new medical images defining the one or more of the image features. For example, the image annotation and the new image annotation data can comprise mark-up data applied to the medical images marking one or more anatomical features, and the non-image annotation and the non-image input can respectively comprise text data. The computer-executable components can further comprise an annotation component that employs the model to generate the new image annotation data for the new medical images given the new medical images and the non-image input.

In various embodiments, the non-image annotation data adheres to one or more criteria (e.g., expert defined clinical criteria tailored to a particular medical image inferencing task and/or the medical images at hand). The system can further facilitate iteratively updating the criteria to improve the bi-directional mappings and the model performance, coupling data annotation and model development in the same framework. For example, the reception component can receive updated non-image annotation data for the medical images that adheres to one or more updated criteria (e.g., expert defined) based on one more errors associated with performance of the model on the new medical images. The machine learning component can further employ one or more second machine learning processes to learn updated bi-directional mappings between updated non-image features included in the updated non-image annotation data and the image features associated with the medical images, and wherein as a result of the one or more second machine learning processes, the machine learning component generates an updated version of model configured to more accurately infer the one or more of the image features associated with new medical images given the new medical images and the non-image input.

In some embodiments, elements described in connection with the disclosed systems can be embodied in different forms such as a computer-implemented method, a computer program product, or another form.

DESCRIPTION OF THE DRAWINGS

FIG. 7 illustrates a block diagram of an example, non-limiting computer implemented method for generating one or more multimodal AI models tailored to specific concepts in medical imaging, in accordance with one or more embodiments of the disclosed subject matter.

FIG. 8 illustrates a block diagram of another example, non-limiting computer implemented method for generating one or more multimodal AI models tailored to specific concepts in medical imaging, in accordance with one or more embodiments of the disclosed subject matter.

DETAILED DESCRIPTION

Figure 1:
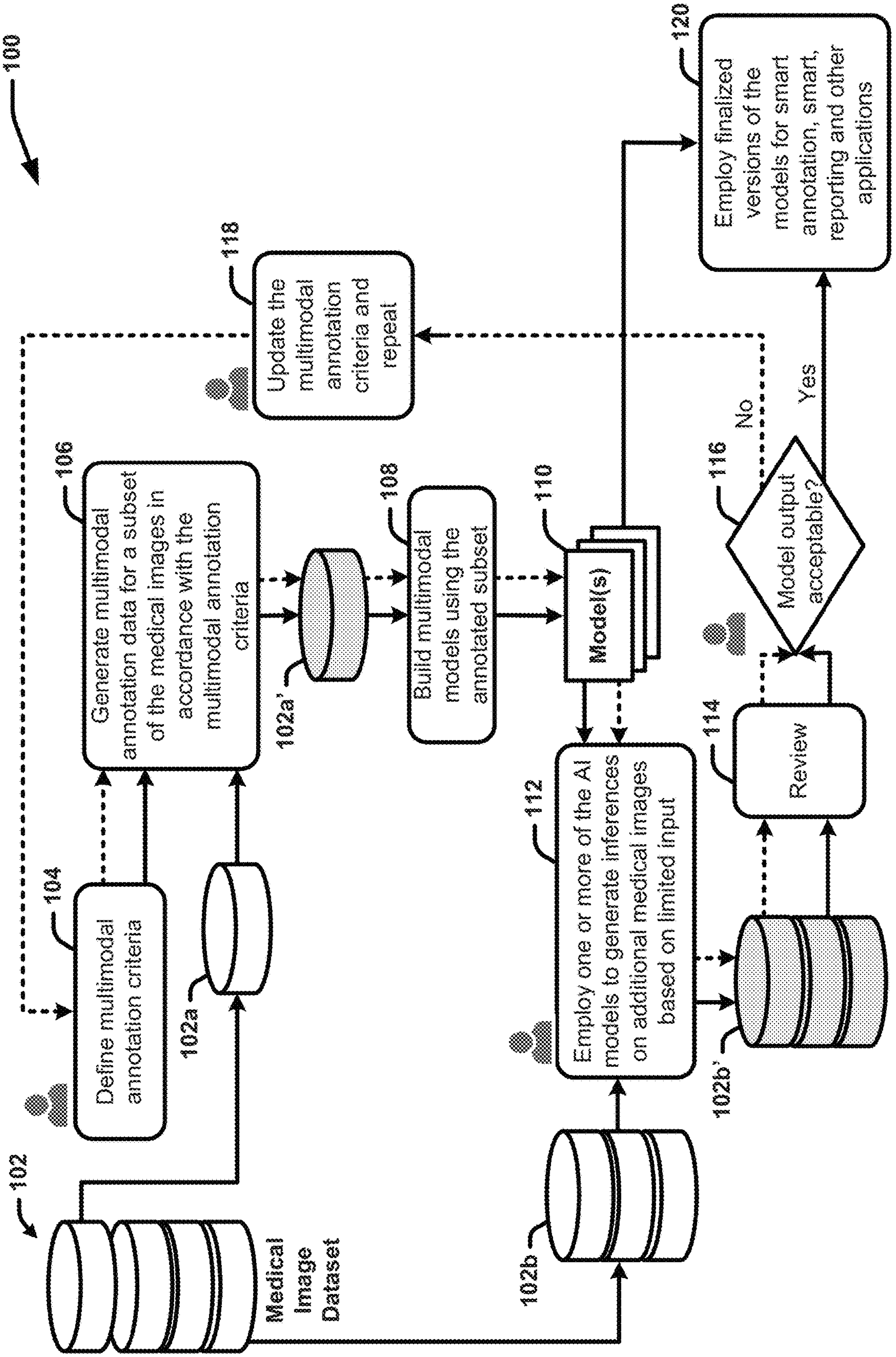
FIG. 1 presents an iterative process for learning multimodal mappings tailored to medical image inferencing tasks, in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Background section, Summary section or in the Detailed Description section.

The subject disclosure provides systems, computer-implemented methods, apparatus and/or computer program products that facilitate an iterative framework for learning multimodal mappings tailored to medical image inferencing tasks. As noted in the Background Section, DL models in the medical imaging domain suffer from three major issues: 1) requirement of large-scale annotated data, 2) asynchronous model development between different development phases (e.g., data curation and annotation, model building, and report generation, 3) and lack of explainability.

In this regard, most DL models used for medical image inferencing tasks require large amounts of annotated medical images for model training. The annotation data typically includes tags or labels associated with the medical images that define or indicate the ground truth (GT) information for the inferencing task of the model to be trained. For example, as applied to lesion detection, the annotation data may include tags applied to the medical images that indicate whether a lesion is present or absent the medical images, and/or mark-up data in the form of a bounding box or another type of visual marking the location and size of lesions present in the medial images.

Current data curation pipelines for obtaining annotated medical images generally involve using clinical expert annotators to review and manually apply annotations to the medical images, which is a time consuming and expensive process. In addition, the existing frameworks for model training and development are slightly disjointed with respect to the data curation phase and the model development phase. In this regard, the expert annotators are typically directed to apply annotations to a medical image dataset tailored for a specific target inferencing task (e.g., diagnosis, segmentation, disease staging, etc.). Once the medical image dataset has been annotated, it is then sent off to a data science team which builds (e.g., trains) the model using the annotated data. Once developed, the model is then deployed for application to new medical images in runtime environments, wherein the end-user is generally only provided the task specific output data that the model is trained to generate, which typically lack explainability with respect to relevant features or factors for which the output results are based. For instance, in furtherance to the lesion detection example, the output data may indicate whether a lesion is present or absent in an input image and/or include graphical mark-up data applied to the medical image indicating the location of the lesion in the input image. However, additional clinical review is needed for generating the radiology report describing the pathology and other relevant information providing a detailed clinical interpretation of the input image and the basis for the model output.

With these issues in mind, the disclosed techniques provide a new framework for data annotation, model development, and deployment utilization in the medical imaging domain enabled by multimodal mappings. In particular, the disclosed techniques are based on multimodal DL learning models that can learn relationships (e.g., multimodal mappings) between input image features and additional input data associated with the input images of a different modality or type, such as text information describing relevant attributes associated with the input images. Based on the learned relationships, a multimodal DL modal can be configured to perform a target inferencing task that can relate information included in non-image input data associated with an input image, such as a text describing the input image, to corresponding image characteristics, and vice versa. One example of such a model developed outside of the medical imaging domain has been used to identify contours of objects in real-world images (e.g., depicting real-world objects, places, things, animals, etc.) given the input image and text a description of the objects.

However, existing multimodal modals of this sort developed for real-world images and real-world objects are not capable of generating any useful outputs as applied to medical images. This is because medical images are much more complex than real-world images and the particular tasks or problems that the models are trained to perform on the medical images require the models to have the intelligence of an expert radiologist tuned to the understand features relevant to the task or problem, type of medical image, the type of anatomy, specialty and so on. This is also because the medical terminology used to describe relevant attributes of medical images not only encompasses complex ontologies unique to the medical field, but also vary for different medical sub-fields, contexts and medical providers, and clinical problems. Accordingly, multimodal modals developed based on learned embeddings between descriptions of real-world objects and images depicting real-world objects cannot be reasonably domain adapted to medical imaging tasks without facing many challenges. These challenges are exacerbated by the existing disjointed data curation and model development frameworks in the medical imaging domain as discussed above.

In one or more embodiments, the disclosed subject matter provides a framework for building (e.g., training) multimodal models configured to perform specific medical image inferencing tasks. As used herein, a multimodal model refers to a model capable of processing two or more different types of input. For example, the two or more different forms of input may include image data (e.g., a medical image) and text data (e.g., text describing the medical image and/or a clinical interpretation of the medical images relevant to a particular task at hand, such as lesion detection, segmentation, classification, etc.). To this end, as applied to medical image inferencing, the two or more different types of input data will generally always include at least image data input, that is the input medical image.

The additional type or types of input data can vary, however in most embodiments will include at least some form of text data. For example, the text data may include text data describing relevant characteristics of the input image for the inferencing task at hand, such as a detailed description of the characteristics of a lesion depicted in the input image as applied to the lesion detection/classification example. To this end, auxiliary text data input can include different types of text data input respectively corresponding to different input types or modalities of the multimodal input data. For example, text data received manually from an expert annotator reviewing the medical image and providing the text input (e.g., in natural language or the like) can be considered one type of additional input data (e.g., in addition to the input medical image itself) of the multimodal input data. Other examples of text input data corresponding to different modalities or types of the multimodal input data can include (but are not limited to), text data extracted from metadata associated with the medical image (e.g., describing image type, image acquisition parameters, resolution, capture position/orientation, etc.), text data extracted from electronic medical record (EMR) data associated with the patient depicted in the medical image, text data extracted from associated laboratory reports, text data extracted from associated clinical reports, and so on. In some embodiments, the additional forms of multimodal input can include related medical images (e.g., past scans for the same patient, similar scans for similar pathologies, etc.). The additional forms of multimodal input may also include sensory data or signal data captured via one or more medical imaging devices, such as signal data that measures various relevant physiological parameters of the patient depicted in the input medical image.

In various embodiments, the multimodal models can be trained to perform bi-directional inferencing. What this means is that the multimodal models can be trained to learn relationships or mappings between input features respectively associated with the different types of multimodal input data and the task at hand during training, such as relationship between image features depicting a lesion in a medical image and textual descriptors describing the lesion for the medical image, as applied to a lesion detection task for example. The multimodal models can further be trained to employ these learned relationships to generate target inference outputs that identify corresponding features of one type or modality given corresponding input features of another type or modality, such as medical images features related to corresponding text input, and/or text features related to corresponding medical image data input. In various embodiments, these multimodal models can be used to perform smart annotation and smart reporting, among other applications.

For example, in some embodiments, the multimodal models can include models trained to identify specific anatomical image features depicted in medical images based on text input describing characteristics of the specific anatomical features. In some implementations of these embodiments, in association with identifying specific anatomical features, the models can also be trained to identify and define the location of the specific anatomical features in the medical images, the contour of the features, and additional detailed characteristics associated with anatomical features, given only limited text input. These types of multimodal models can be used to accelerate the annotation process by automatically generating annotation data (e.g., bounding box data, mask data, etc.) for training medical images that defines the location, size, counter etc. of one or more relevant anatomical structures to the task at hand given the medical images give the medical images and only a text description of the one or more anatomical structures. The annotation data can also include additional, automatically generated text data and/or other types of multimodal data features mapped to the text description (and/or portions thereof) and/or the corresponding anatomical structures for the task at hand.

In another example embodiment, the multimodal models can include models configured to perform bi-directional querying, such as finding medical images that satisfy a text query (e.g., "Fetch medical images that contain lesions of type "xyz".). To this end, unlike traditional querying techniques, the trained models do not use tags or labels associated with the medical images, but inheritably understand the relationships between the image features as extracted from the medical images themselves the corresponding text descriptors associated with the extracted features as a result of learning the mappings during training. In another example, the multimodal models can include models configured to generate textual information describing relevant image features depicted in an input medical image based on learned mappings between the relevant image features and text features associated with the relevant features. In accordance with this example, the multimodal models can be used to perform smart reporting by generating detailed textual descriptions providing clinical interpretations of a medical image and relevant related auxiliary data (e.g., EMR data, laboratory data, similar scans, etc.).

In order to generate robust multimodal models with such capabilities in medical imaging, the learned mappings between the image features of respective medical images and the additional multimodal data features (e.g., text data and/or other forms of auxiliary data) account for highly specific clinical concepts, features and ontologies tuned to the types of the medical image and a particular context of clinical interpretation, that is a particular medical image inferencing task. To facilitate this end, the disclosed framework leverages the clinical expertise of the expert annotators and allows them to define and generate the additional multimodal data features of relevance to a target inferencing task and medical image dataset in accordance with the clinical concepts, features and ontologies they consider relevant and useful to the target inferencing task and/or to providing a robust, detailed clinical interpretation of the medical images in the dataset.

In addition, the disclosed framework combines the data annotation and model development phases in an iterative framework that leverages the expertise of the clinical annotators to refine and update the additional multimodal data features of relevance that control the learned mappings between the medical image features and the additional multimodal data features as the model is being built (e.g., based on the performance of the model during training). For example, in some embodiments, the annotation pipeline can involve having an expert annotator (e.g., a radiologist or another person capable of reading and interpreting medical images in a clinical context with appropriate expertise for the target inferencing task at hand) perform "strong" annotation of a subset of the medical images included in a training dataset. In this context, "strong" annotation refers to manually reviewing the medical images and providing not only conventional GT annotation data for a target inferencing task (e.g., segmentation, diagnosis, classification etc.), such as mark-up data (e.g., bounding box data, mask data, or the like) marking an anatomical feature of interest (as applied to segmentation and/or detection tasks), text data defining a classification of the anatomical feature of interest (e.g., as applied to classification task), but further providing additional annotation data in the form of text (or speech to-text, gesture to text, etc.) describing relevant attributes of each medical image in accordance with specific clinical concepts, features and ontologies tuned to the types of the medical image and the particular context of clinical interpretation, (e.g., one or more target medical image inferencing tasks). To this end, “strong” annotation also refers to generating multimodal annotation data for a medical image. Importantly, in association with applying the multimodal annotation data to the subset of the medical images, the expert annotator can constrain the additional annotation data (e.g., additional to the GT data) in accordance with defined criteria (e.g., clinical concepts, clinical ontologies, clinical terms, etc.) determined by the expert to be relevant to the medical images and the target inferencing task (or tasks in some implementations).

Once the initial subset of medical images have been strongly annotated with a combination of conventional GT annotation data and additional descriptive text data (and/or other forms of non-image annotation data), the annotated medical images are used to learn the bi-directional between the relevant image features in the medical images and the additional input data features (e.g., textual terms and phases, etc.) for the task at hand, which in turn are used to train one or more multimodal models to perform the task and/or additional bi-directional inferencing tasks associated with the medical images. For example, in various embodiments, the learned mappings can be used to generate a model configured to generate a mask (a bounding box or the like) that defines the location and contour of a lesion in an input medical image given the medical image as input and a text description of the lesion. In accordance with this example (and additional examples described infra), the bi-directional model trained on the strongly annotated samples can then be used to more efficiently annotate the rest of the medical images included in the training dataset with mask annotation data and/or additional correlated multimodal input data using only limited text input.

Further, the iterative framework allows the expert annotator to review preliminary results of the version of bi-directional model trained based on the strongly annotated data samples). For instance, in furtherance to the lesion/mask example, the expert annotator can review the mask generated by the model on the additional medical images included in the training dataset (e.g., or portions thereof) based on the provided descriptive text input. Based on observed, errors in the model output on the new images using the text input, the annotation pipeline allows the expert annotator to refine or update the clinical criteria used to control the additional strong annotation data (e.g., the text input) and revise the multimodal data applied to the subset of medical images according to the updated criteria. In other words, the expert annotator can add additional descriptors, change terms used, change phrases used and the like. The subset of medical images with the updated multimodal annotation data is then used to refine or update the learned mapping and the model, and this process can be repeated iteratively until convergence is achieved. In this regard, with the disclosed techniques, the expert annotator can control the annotation data that controls the performance of the model prior to deployment of the model in runtime environments.

In this regard, the disclosed subject matter proposed provides tools that tackle both smart annotation and smart reporting for AI based medical image analysis. These tools can provide several benefits including (but not limited to): 1) utilizing lesser time of experts for training data annotation, 2) faster and more robust AI model building for complex clinical tasks, 3) immersion of expert-driven concepts in DL models, and 4) smart reporting in clinical language defined by experts. Consequently, the disclosed tools enable faster transitions of AI products to market, increased chances of adoption owing to explainability, and ultimately improved patient outcomes.

The term “image data,” is used herein to refer to one or more images, image data structures (e.g., image files in any format), and/or video data composed of picture elements (e.g., pixels) capable of being rendered via a display as a visual data object. For example, the term image data can refer to one or more digital images, native images, synthetic images, or the like. The term image data can also refer to a portion of an image, mark-up data (e.g., visual marking, bounding boxes, labels, lines, masks, segmentation masks, etc.), an augmented image, a graphical image, a sinogram image, or another type of image construct comprising visual elements capable of being rendered via a display.

The term “medical image data” is used to refer to image data that depicts one or more anatomical regions of a patient. Reference to a medical image or medical image data herein can include any type of medical image associated with various types of medical image acquisition/capture modalities. For example, medical images can include (but are not limited to): radiation therapy (RT) images, X-ray (XR) images, digital radiography (DX) X-ray images, X-ray angiography (XA) images, panoramic X-ray (PX) images, computerized tomography (CT) images, mammography (MG) images (including a tomosynthesis device), a magnetic resonance imaging (MRI) images, ultrasound (US) images, color flow doppler (CD) images, position emission tomography (PET) images, single-photon emissions computed tomography (SPECT) images, nuclear medicine (NM) images, and the like. Medical images can also include synthetic versions of native medical images such as augmented, modified or enhanced versions of native medical images, augmented versions of native medical images, and the like generated using one or more image processing techniques. In some embodiments, the term “image data” can include the raw measurement data (or simulated measurement data) used to generate a medical image (e.g., the raw measurement data captured via the medical image acquisition process).

The term “non-image data” is used herein to refer to any type of data that excludes image data. In this regard, the term “non-image data” can include text data (e.g., a text data file in any text data type format), audio data (e.g., an audio file in any type of audio file format), signal data generated via one or more machines or sensors, or another type of data format excluding image data.

The terms “algorithm” and “model” are used herein interchangeably unless context warrants particular distinction amongst the terms. The terms “artificial intelligence (AI) model” and “machine learning (ML) model” are used herein interchangeably unless context warrants particular distinction amongst the terms. Reference to an AI or ML model herein can include any type of AI or ML model, including (but not limited to): deep learning (DL) models, neural network models, deep neural network models (DNNs), convolutional neural network models (CNNs), generative adversarial neural network models (GANs), transformer models, and the like. An AI or ML model can include supervised learning models, unsupervised learning models, semi-supervised learning models, combinations thereof, and models employing other types of ML learning techniques. An AI or ML model can include a single model or a group of two or more models (e.g., an ensemble model, chained models, or the like).

The term "image inferencing model" is used herein to refer to an AI/ML model adapted to perform an image processing or analysis task on image data. The image processing or analysis task can vary. In various embodiments, the image processing or analysis task can include, (but is not limited to): a segmentation task, an image reconstruction task, an object recognition task, a motion detection task, a video tracking task, an optical flow task, and the like. The image inferencing models described herein can include two-dimensional (2D) image processing models as well as three-dimensional (3D) image processing models. The image processing model can employ various types of AI/ML models (e.g., deep learning models, neural network models, deep neural network models, DNNs, CNNs, GANs, etc.). The terms "image inferencing model," "image processing model," "image analysis model," and the like are used herein interchangeably unless context warrants particular distinction amongst the terms.

The term "image-based inference output" is used herein to refer to the determination or prediction that an image processing model is configured to generate. For example, the image-based inference output can include a segmentation mask, a reconstructed image, an adapted image, an annotated image, a classification, a value, or the like. The image-based inference output will vary based on the type of the model and the particular task that the model is configured to perform. The image-based inference output can include a data object that can be rendered (e.g., a visual data object), stored, used as input for another processing task, or the like. The outputs can be in different formats, such as for example: a Digital Imaging and Communications in Medicine (DICOM) structured report (SR), a DICOM secondary capture, a DICOM parametric map, an image, text, and/or JavaScript Object Notation (JSON). The terms "image-based inference output", "inference output" "inference result" "inference", "output", "result," "predication", and the like, are used herein interchangeably unless context warrants particular distinction amongst the terms.

As used herein, a "medical imaging inferencing model" refers to an image inferencing model that is tailored to perform an image processing/analysis task on medical image data. For example, the medical imaging processing/analysis task can include (but is not limited to): disease/condition classification, disease region segmentation, organ segmentation, disease quantification, disease/condition staging, risk prediction, temporal analysis, anomaly detection, anatomical feature characterization, medical image reconstruction, and the like. The terms "medical image inferencing model," "medical image processing model," "medical image analysis model," and the like are used herein interchangeably unless context warrants particular distinction amongst the terms.

Embodiments of systems and devices described herein can include one or more machine-executable (i.e., computer-executable) components or instructions embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described. These computer/machine executable components or instructions (and other described herein) can be stored in memory associated with the one or more machines. The memory can further be operatively coupled to at least one processor, such that the components can be executed by the at least one processor to perform the operations described. In some embodiments, the memory can include a non-transitory machine-readable medium, comprising the executable components or instructions that, when executed by a processor, facilitate performance of operations described for the respective executable components. Examples of said and memory and processor as well as other suitable computer or computing-based elements, can be found with reference to FIG. 9 (e.g., processing unit 904 and system memory 906 respectively), and can be used in connection with implementing one or more of the systems or components shown and described in connection with FIG. 1, or other figures disclosed herein.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Turning now to the drawings, FIG. 1 presents an iterative process 100 for learning multimodal mappings tailored to medical image inferencing tasks, in accordance with one or more embodiments of the disclosed subject matter. Process 100 combines the training data curation phase and the model building (e.g., model training) phases into the same framework, leveraging the expertise of one or more expert annotators. In various embodiments, the disclosed techniques can be performed in association with using a single expert annotator such that the learned embeddings used to generate one or more bi-directional ML models are tailored to the specific natural language and clinical expertise of the specific expert annotator. With these embodiments, process 100 (and additional processes and systems described herein) can be used to generate "personal" AI models that are tuned to process input data and generate corresponding output data that reflects the natural language, dialect, and clinical expertise of particular medical professional. Additionally, or alternatively, the disclosed techniques can be performed in association with using a plurality of different expert annotators collaborating their expertise and clinical knowledge together. In this regard, elements of process 100 involving obtaining manual input from one or more annotators are indicated by the (cropped) human icon. Reference to "the annotator," the "expert annotator," the "annotating entity," or the like is assumed to be understood to correspond to a single person, but it should be appreciated that the annotator may include two or more different people.

Process 100 is described in association with generating multimodal annotation data for a medical image dataset 102. In various embodiments, the medical image dataset 102 corresponds to a training dataset comprising a plurality of medical images that need to be annotated with GT information for a particular target medical image inferencing task. The type of the medical images included in the training dataset and the particular medical image inferencing task can vary. However, as applied to medical image inferencing models, the medical images that make up a training dataset generally include different variants of the same type of medical images (e.g., same modality, same or similar anatomical regions, same or similar pathologies, etc.), wherein the different variants are typically based on different subjects or patients from which the medical images were captured.

By way of example, process 100 is described in the context of annotating ultrasound images of the chest in association with generating a lesion segmentation model configured to detect and segment lesions depicted in the images. In accordance with this example, all of the medical images included in the medical image dataset 102 would include different ultrasound images of the chest, such as different images captured from different subjects providing different examples of lesions. However, it should be appreciated that this specific use case is merely exemplary and that process 100 and the techniques described herein can be applied to any types of medical images and any types of medical image inferencing tasks. In addition, the target medical image inferencing task can include or correspond to a "main" task of an AI model to be trained on the annotated training images. As described in greater detail below, the annotated training images can also be used to train the AI model and/or one or more separate AI models to perform additional bi-directional inferencing tasks based on the learned embeddings between image features extracted from the medical images and additional features included in the multimodal annotation data.

In accordance with process 100, at 104, the expert annotator can define multimodal annotation criteria that controls the multimodal annotation data to be applied to at least some of the medical images included in the medical image dataset 102. For example, in accordance with process 100, the annotator can perform strong annotation on a small subset 102*a* of the medical images included in the medical image dataset 102. In some embodiments, the strongly annotated data samples can then be used to generate one or more bi-directional models (e.g., one or more models 110) configured to automatically infer and apply annotation data to the additional medical images 102*b* included in the medical image dataset 102 in a much more efficient and automated fashion, referred to herein as "smart annotation," as explained in greater detail below.

The multimodal annotation criteria defined at 104 can control and/or guide the type and contents of the multimodal annotation data to be applied to the respective medical images included in the subset 102*a*. The term "multimodal annotation data" is used herein to refer to two or more different types of modalities of annotation data. In various embodiments, the types of the multimodal annotation data can include a first type corresponding to conventional GT annotation data for a specific target medical image inferencing task. For example, as applied to lesion detection, the first type of multimodal data may include mark-up data applied to respective medical images in the subset 102*a* marking any lesions observed in the medical images, such as graphical bounding boxes drawn around the lesions that reflect the size and geometry or contours of the lesions as illustrated in FIG. 2.

Figure 2:
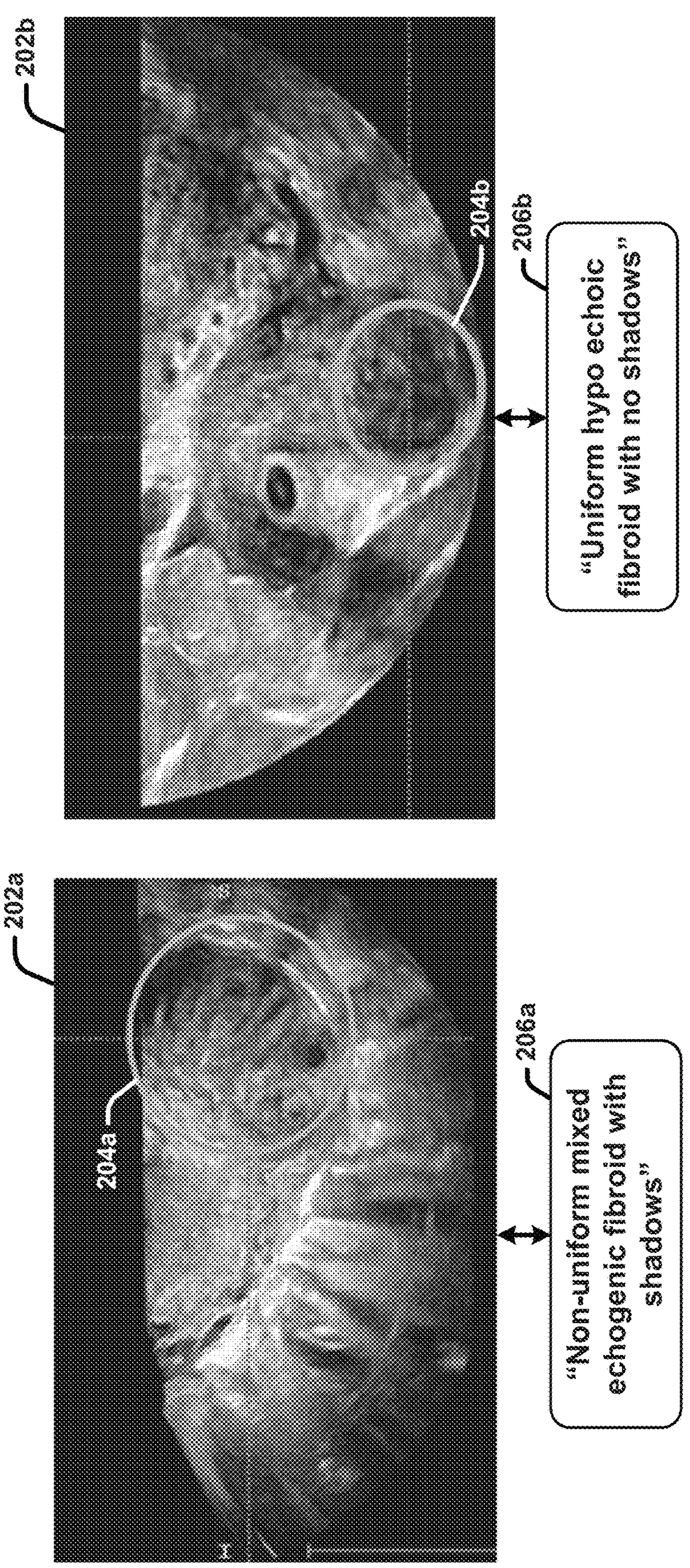
FIG. 2 presents examples of multimodal annotation data applicable to medical images, in accordance with one or more embodiments of the disclosed subject matter.

In this regard, with reference briefly to FIG. 2, FIG. 2 presents examples of multimodal annotation data applicable to medical images, in accordance with one or more embodiments of the disclosed subject matter. FIG. 2 presents two different example ultrasound images (e.g., image 202*a* and image 202*b*) of the chest respectively comprising lesions. In this example, the lesions are marked on the respective images with graphical bounding boxes 204*a* and 204*b* (noting that the term "bounding box" herein can encompass any geometrical shape, (i.e., circular) and is not limited to rectangular shaped boxes). These bounding boxes 204*a* and 204*b* correspond to conventional GT image annotation data that is used to annotate medical images for ML tasks that involve automatically detecting target anatomical features of interest (in this case lesions), performing segmentation (e.g., generating segmentation masks defining the location, size and/or contours of anatomical features of interest), and various other medical image inferencing tasks. Other forms of visual or graphical GT annotation data that may be applied to medical images for various types of inferencing tasks include calipers or markers (e.g., symbols, lines, etc.) that mark anatomical features of interest and/or relative positions of two or more anatomical features of interest. In some implementations, the target anatomical features of interest may not be "anatomical" features but artifacts to be distinguished from real anatomical features and/or to be removed by the model (e.g., as applied to an artifact removal model), and/or areas/regions of an image associated with quality issues (e.g., streaks, poor resolution, etc.), to be enhanced by the model (e.g., as applied to medical image quality enhancement models). In this regard, any type of visual mark-up annotation data applied to medical images is considered "image annotation data" for purposes of the disclosed subject matter.

With reference again to FIG. 1 along with FIG. 2, the first type of annotation data is not restricted to graphical mark-up data (i.e., image annotation data) such as that described above. For example, in some implementations, depending on the target medical inferencing task, the GT annotation information may include text data (i.e., non-image annotation data) that merely indicates whether a particular medical condition is present or absent in the images. In this regard, the conventional GT annotation data corresponding to the first type of annotation data can vary based on the target medical image inferencing task.

In some embodiments, the first type of annotation data may be predefined for a given medical image dataset 102 and a target inferencing task. In other embodiments, at 104, the expert annotator can define the target inferencing task and/or the criteria of the first type of annotation data. Generally, because the first type of annotation data corresponds to the GT information, which directly corresponds to the specific output information that a ML model will be trained to predict, the first type of annotation data can be considered structured data that adheres to relatively structured or strict criteria.

Additionally, or alternatively, the multimodal annotation data to be applied to the subset 102*a* can include one or more additional types of annotation data. In various embodiments, the one or more additional types of annotation data can include a second type of annotation data corresponding to manually applied text data (i.e., non-image annotation data) describing relevant clinical and/or non-clinical features associated with the medical images and the target inferencing task. For example, the text data can comprise unstructured text input provided by the annotator describing an expert clinical interpretation of the medical images included in the subset 102*a* using a natural language description.

In this regard at 104, the annotator can define the relevant clinical concepts or criteria to be described by the annotator using unstructured text input, which may be received via any suitable input mechanism, such as via a keyboard, a touchscreen, speech to text, gesture to text, or the like. To this end, process 100 allows the expert to determine and define the types of textual information that is or may be relevant to the main inferencing task in addition to the GT annotation data. For instance, the expert defined criteria that may control such text input can include defined categories of clinical and/or non-clinical information. Some example categories relevant to the lesion detection task may include but are not limited to, regions of interest, lesion types, lesion characteristics, a description of the anatomy, and image artifacts. To this end, the term "clinical criteria," as used herein refers to criteria that is directly related to the anatomy and physiology of a living body (e.g., human body, animal body, or another living being) including all its components, processes, conditions affecting it, and procedures performed upon it. The term "non-clinical" criteria is used herein to refer to any criteria excluding clinical criteria. Examples of non-clinical criteria can include but are not limited to, information describing or pertaining to medical image acquisition processes (e.g., acquisition parameters), subject demographics (e.g., age, gender, location, socioeconomic status), information describing or pertaining to image quality (e.g., coloration, artifacts, resolution, blur, etc.), information describing or pertaining to subject behaviors, and the like.

It should be appreciated that particular clinical and non-clinical concepts that are or may be relevant to the main inferencing task can vary. In addition, the particular clinical and non-clinical concepts used to define and control the natural language text description annotation data are not limited to those that are relevant to the main inferencing task. In this regard, the second type of multimodal annotation data can include essentially unlimited descriptive text information for the subset 102*a* of medical images providing a comprehensive description of clinical and non-clinical image features depicted in the medical images which may be used for other tasks in addition to or alternative to the main task.

In some embodiments, the one or more additional types of annotation data can include other forms of text input data corresponding to different modalities or types of the multimodal input data. Some examples can include (but are not limited to), text data extracted from metadata associated with the medical image (e.g., describing image type, image acquisition parameters, resolution, capture position/orientation, etc.), text data extracted from electronic medical record (EMR) data associated with the patient depicted in the medical image, text data extracted from associated laboratory reports, text data extracted from associated clinical reports, and so on. For example, the EMR text data can comprise patient information regarding respective patients represented in the medical images as included in one or more EMR data files. In some embodiments, the additional forms of multimodal input can include related medical images (e.g., past scans for the same patient, similar scans for similar pathologies, etc.). The additional forms of multimodal input may also include sensory data or signal data captured via one or more medical imaging devices, such as signal data that measures various relevant physiological parameters of the patient depicted in the input medical image. To this end, the amount, type and contents of the multimodal annotation data applied to the subset 102*a* can vary and encompass essentially any type of information that may be included in a comprehensive radiology report for the medical images.

Continuing with process 100, at 106, the expert annotator can generate the multimodal annotation data for respective medical images included in the subset 102*a* in accordance with the multimodal annotation criteria defined at 104. To facilitate this end, the annotator can employ a suitable medical imaging application that allows the annotator to view the medical images included in the subset as displayed via a graphical user interface (GUI), apply mark-up annotation data to the medical images (e.g., using existing medical image mark-up annotation software), provide unstructured texts input describing relevant image features (e.g., via free form data entry, via speech which is then converted to text, of via another suitable input mechanism), and optionally generate and/or provide (e.g., import, upload, provide links to, etc.) additional input in the form of relevant medical records, laboratory reports, metadata, related medical images, and the like.

For example, as applied to a lesion segmentation task being the main inferencing task, let's assume the multimodal annotation criteria includes first criteria defining a first type of annotation data to be applied to the medical images that corresponds to providing GT image annotation data to the medical images marking any observed lesions with bounding boxes. Let's further assume that the multimodal annotation criteria includes second criteria describing a second type of annotation data to be applied to the medical images, the second type of annotation data comprising unstructured text data provided in the annotator's natural language and the second criteria including descriptive information that adheres to the following two categories, 1) a description of the type of lesion and 2) a description of the characteristics of the lesion. FIG. 2 provides examples of such multimodal annotation data that applied to example images 202*a* and 202*b* in accordance with the first and second criteria. For example, as described above, the circular bounding boxes 204*a* and 204*b* correspond to the first type of annotation data (i.e., image annotation data) and the text descriptions 206*a* and 206*b* respectively correspond to the second type of annotation data. In this example, the text description applied by the expert annotator describes the observed lesion in image 202*a* as being a "non-uniform mixed echogenic fibroid with shadows," and the text description applied for the observed lesion in image 202*b* describes the lesion as being a "non-uniform mixed echogenic fibroid with shadows." It should be appreciated that reference to "applying" text data to a medical image in accordance with the disclosed subject matter includes any mechanism of associating the text data with the corresponding image. For example, the text data may be "applied" as a separate text file, metadata, or the like.

In some implementations, in association with providing text input in accordance with the defined criteria or categories for the types of text input defined by the annotator categories, the annotator can indicate the particular category being described. For example, the expert annotator can indicate "the regions of interest depicted include . . . ," "the type of the lesion is . . . ," "the characteristics of the lesion include . . . ," and so on. These categorical prompts can add context for the medical terms associated therewith, which can facilitate learning contextual embeddings of the medical terms used by the annotator with respect to particular context in which they are used. Contextual embeddings assign each word a representation or meaning based on its context, thereby capturing uses of words across varied contexts. To this end, the particular context in which terms they are used by the annotator reflects the specific type of medical images being evaluated and the contents (i.e., image features) of the images, as well as the particular target medical image inferencing task. The contextual embeddings of the terms can thus facilitate learning the mappings between the terms to corresponding medical images and/or particular image features (e.g., anatomical features) included in the medical images.

Although the example text descriptions shown in FIG. 2 are relatively concise, it should be appreciated that the amount of descriptive annotation text data applied by the expert annotator can vary, and that the text descriptions provided in FIG. 2 are merely exemplary. In addition, although generating the multimodal annotation data at 106 is a manual task that requires the expert annotate to carefully review and apply strong annotation data to individual medical images, process 100 limits this strong annotation task to only a subset 102*a* of the medical images included in the medical image dataset 102, and enables the remaining majority of the medical images (e.g., the additional medical images 102*b*) to be annotated using a smart annotation model trained on the strong annotation data applied to the subset 102*a*, as described in greater detail below.

Continuing with process 100, the subset 102*a* of medical images with the strong. multimodal annotation data applied thereto is represented in process 100 as the annotated subset 102*a*'. At 108, the annotated subset 102*a*' of medical images is used to build (e.g., train) one or more AI models 110. In particular, at 108, the annotated subset 102*a* of medical images can be provided (e.g., sent, transmitted, accessed, etc.) to a machine learning system (i.e., computing system 600 or a similar system) configured to employ one or more machine learning processes to train one or more multimodal models (e.g., models 110) to perform the main inferencing task and/or one or more additional bi-directional inferencing tasks. For example, in various embodiments, the one or more machine learning processes can involve employing/training one or more transformer models and/or one or more task-specific decoder models to learn the bi-directional mappings using the annotated subset 102*a*', and training a task-specific decoder 414 in association with training the one or more transformer models and/or one or more task-specific decoder models to perform a specific bi-directional inferencing task on the medical images using the learned mappings. For example, the one or more transformer/task-specific decoder models may include or correspond to one or more contrastive language image pre-training CLIP) models and/or a CLIP-SEG (CLIP-segmentation model) trained to perform segmentation of one or more specific anatomical features of interest associated with a specific type of input medical images.

In this regard, at 108 the one or more multimodal models 110 can be trained to learn relationships or mappings between input features respectively associated with the different types of multimodal input data and image features respectively extracted from the input medical images, such as relationship between image features depicting a lesion in the example lesion medical images and textual descriptors describing the lesion for the medical image, as applied to a lesion segmentation task for example. To this end, the relationships or mappings can be tailored to the specific target or main inferencing task, as the multimodal data is tailored to the main inferencing task. The one or more multimodal models 110 can further be trained to employ these learned relationships to generate target inference outputs that identify corresponding features of one type or modality given corresponding input features of another type or modality. such as medical images features related to corresponding text input, and/or text features related to corresponding medical image data input. In various embodiments, these multimodal models can be used to perform smart annotation and smart reporting, among other applications.

For example, in some embodiments, the one or more multimodal models 110 can include a model trained to identify specific anatomical image features depicted in medical images based on text input describing characteristics of the specific anatomical features. This model can be tailored to the specific type of medical images included in the subset 102*a* and the relevant features described, which may be tailored to a specific medical image inferring task (e.g., lesion segmentation for example). These techniques can be used to generate various different versions of the model tailored to different types of medical images (e.g., modality, anatomical region or regions depicted, pathology depicted, etc.) and relevant clinical and non-clinical features of the images described.

In some implementations of these embodiments, these types of multimodal models can be used to perform bi-directional querying, such as finding medical images that satisfy a text query (e.g., "Fetch medical images that contain lesions of type "xyz".). To this end, unlike traditional querying techniques, the trained models do not use tags or labels associated with the medical images, but inheritably understand the relationships between the image features as extracted from the medical images themselves the corresponding text descriptors associated with the extracted features as a result of learning the mappings during training. In another example, these types of multimodal models can include models configured to generate textual information describing relevant image features depicted in an input medical image based on learned mappings between the relevant image features and text features associated with the relevant features. In accordance with this example, the multimodal models can be used to perform smart reporting by generating detailed textual descriptions providing clinical interpretations of a medical image and relevant related auxiliary data (e.g., EMR data, laboratory data, similar scans, etc.). For example, the model can be configured to extract one or more image feature vectors from an input medical image and generate text output data describing the contents of the medical image based on learned mappings between the image feature vectors and the text data associated with the respective image feature vectors.

Still in other implementations, these types of multimodal models can be used to perform smart annotation. For example, in some embodiments, in association with identifying specific anatomical features based on additional non-image data (e.g., text data), the models can also be trained to identify and define the location of the specific anatomical features in the medical images, the contour of the features, and additional detailed characteristics associated with anatomical features, given only limited text input. These types of multimodal models can be used to accelerate the annotation process by automatically generating annotation data (e.g., bounding box data, mask data, etc.) for training medical images that defines the location, size, counter etc. of one or more relevant anatomical structures to the task at hand given the medical images give the medical images and only a text description of the one or more anatomical structures. The annotation data can also include additional, automatically generated text data and/or other types of multimodal data features mapped to the text description (and/or portions thereof) and/or the corresponding anatomical structures for the task at hand.

For example, as applied to the example lesion segmentation task being the main inferencing task, at 108 the machine learning system can train a lesion segmentation model to detect and segment (e.g., via generating a bounding box or mask around lesions) in input medical images using the annotated subset 102*a*' of training images. Typically, such a model is trained in a supervised manner by training a deep learning model to identify lesions and their contours as depicted in the training images using GT mark-up annotation data associated therewith defining the boundaries or contours of the lesions. Once trained, the model should be configured to receive a new input medical image corresponding to the training images (e.g., same modality and anatomical region depicted) as input, and generate segmentation data (e.g., a bounding box, a mask or the like) defining the contour of a lesion depicted in the new medical image.

However, in addition to training the model to detect and segment the lesions based on such GT mark-up annotation data associated therewith, the disclosed techniques train the model to learn mappings between non-image input features (i.e., textual terms and phrases and/or other forms of multimodal annotation data) and corresponding image features. For example, as applied to the lesion segmentation model example, the mappings can include mappings between image features of the lesions and their contours within the training images, and textual descriptors of the lesions, such as the example text descriptions 206*a* and 206*b* presented in FIG. 2. These mappings can further be used to train one or more AI models 110 to perform various bi-directional inferencing tasks.

For example, in some embodiments, as applied to the lesion segmentation example, these mappings can be used to train the lesion segmentation model to use textual descriptions of lesions observed in new input images as additional input (e.g., in addition to the new input images along) to facilitate detecting and segmenting any lesions depicted in the new images. To this end, the additional text input describing the lesions can improve the accuracy of the segmentation model. For example, the lesion segmentation model can be configured to receive an input medical image and text description of a lesion observed in the input image and generate a bounding box or mask around the lesion, as illustrated in FIG. 3

Figure 3:
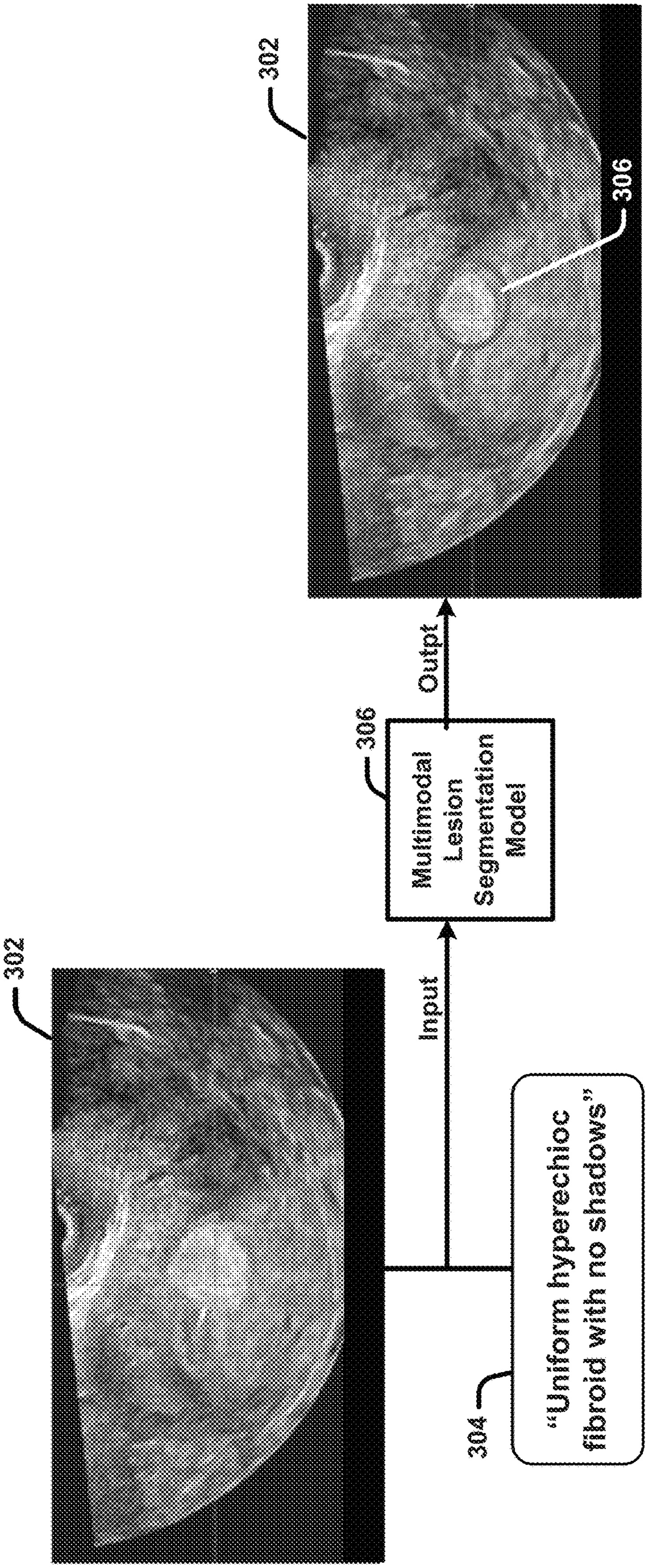
FIG. 3 presents an example multimodal lesion segmentation model, in accordance with one or more embodiments of the disclosed subject matter.

With reference briefly to FIG. 3, FIG. 3 illustrates an example multimodal lesion segmentation model 306 corresponding to the lesion detection model described above. For example, the multimodal lesion segmentation model 306 corresponds to a trained version of a lesion segmentation model trained on training data samples corresponding to the medical images depicted in FIG. 2 with the paired GT mark-up data and the additional text descriptions of the lesions. As illustrated in FIG. 2, the multimodal lesion segmentation model 306 is configured to receive as input, a new input medical image 302 corresponding to the training images (e.g., an ultrasound image of the chest) and a text description 304 of a lesion observed in the input image. The output of the multimodal lesion segmentation model 306 includes a bounding box 304 overlayed onto the medical image 302 encircling the boundary of the lesion as detected in the medical image 302.

With reference to FIGS. 1-3, in accordance with some embodiments of disclosed techniques, the additional text input describing the lesions can be used to train a preliminary version of the multimodal lesion segmentation model 306 that can detect and segment lesions using only the (small) annotated subset 102*a* of training images. In this regard, the additional text input can enable the preliminary version of the lesion detection model to detect and segment the lesions using significantly less training time as compared to training the segmentation model on the entire training dataset. In some implementations of these embodiments, the preliminary version of the multimodal lesion segmentation model 306 can be used by the expert annotator to generate GT segmentation data (e.g., bounding boxes, masks, or the like) for the additional medical images 102*b* of the medical image dataset 102 using text prompts as additional input, a process referred to herein as "smart annotation."

In this regard, continuing with process 100, at 112, the expert annotator can employ one or more of the AI models 110 to generate inferences on the additional medical images based on limited input. For example, in accordance with embodiments in which the one or more AI models 110 correspond to smart annotation models configured to generate GT annotation data for medical images as facilitated based on text prompts (and/or other types of additional multimodal input data), at 112, the expert annotator can employ the smart annotation model to generate GT annotation data for the additional medical images 102*b* (or a portion thereof) based on text prompts provided by the annotator. For example, let's assume the one or more models 110 includes the multimodal lesion segmentation model 306 that has been trained on the annotated subset 102*a*, wherein respective data samples included in the annotated subset 102*a* correspond to the example medical images 202*a* and 202*b* depicted in FIG. 2 with the paired GT mark-up data and the additional text descriptions of the lesions. In accordance with this example, at 112 the expert annotator can review/view the additional medical images (or a portion thereof), provide only a text description of the lesions observed, and employ the multimodal lesion segmentation model 306 to generate the GT bounding box annotation data for the additional medical images as illustrated in FIG. 3. To this end, the expert annotator does not need to perform the "strong" annotation process on the majority of the training images can thus much more efficiently generate the GT mark-up data for the majority of the training images using the text prompts as input. In accordance with this example, the rest (or a portion thereof) of the training images with the model generated GT mark-up data are represented in FIG. 1 as annotated additional medical images 102*b*'.

It should be appreciated that the lesion segmentation model implementation is merely exemplary. In this regard, process 100 can be used to generate preliminary versions of other types of models 110 configured to generate other types of GT annotation data for other types of medical images based on limited input (e.g., text prompts and/or other types of multimodal input). To this end, the models 110 can include other types of smart annotation models configured to generate other types of GT annotation data and/or for other types medical images and inferencing tasks. To this end, the annotated additional images 102*b*' are not restricted to lesion image with GT bounding box data applied thereto and can correspond to any type of medial images with GT annotation data applied thereto via a smart annotation model generated in accordance with the disclosed techniques. Additionally, as described in greater detail below, the one or more models 110 can perform other bi-directional inferencing task aside from smart annotation.

Continuing with process 100, at 114, the expert annotator can review the inference outputs generated by the model on the additional medical images. For example, as applied to smart annotation, the expert annotator can review the annotated additional medical images 102*b*' with the GT annotation data applied thereto by the smart annotation model (one or more of the models 110). For example, the expert annotator can review the results of the smart annotation model, such as the automatically generated GT lesion bounding boxes in accordance with the multimodal lesion segmentation model example. To this end, the expert annotator can assess the performance of the smart annotation model and at 116, determine whether the model output data is acceptable. For example, continuing with the multimodal lesion segmentation model example, the expert annotator can assess whether the model generated bounding boxes are sufficiently accurate as generated based on the annotator's text prompts. It should be appreciated that this can involve using the model to generate the GT mark-up data for a portion of the additional medical images 102*b* and thereafter assess the performance of the model on the portion of the additional medical images at a time 102*b*. In association with evaluating the performance of the model at 116, the expert annotator can determine whether the performance of the model is unacceptable or acceptable based on results generated for the portion of the additional medical images 102*b* or the entirety of the additional medical images 102*b*.

At 116, if the expert annotator determines that the performance of the model is acceptable, in some embodiments, the versions of the models 110 trained on the initial strong annotated subset 102*a* can be considered ready for deployment and thus finalized. With these embodiments, process 100 can continues to 120 wherein the finalized versions of the one or more models 110 can be employed for smart annotation, smart reporting and other applications. In this regard, the term "smart-annotation" is used herein to refer to an process for generating annotation data for one or more medical images using a trained version of one or more ML or AI models (e.g., one or more models 110) configured to infer and generate at least some of the annotation data. Similarly, the term "smart reporting" is used herein to refer to a process for generating a medical or clinical report using a trained version of one or more ML or AI models (e.g., one or more models 110) configured to infer and generate at least some of the information included in the medical or clinical report.

However, at 116, if the expert annotator determines that the performance of the model is not acceptable, in some embodiments, the expert annotator can facilitate updating/retraining the model to achieve better performance by adjusting or updating the multimodal annotation criteria at 118 and repeating process 100 following the dashed arrow flow. In this regard, the expert annotator can update the multimodal annotation criteria such that the type and/or contents of the multimodal annotation data applied to the subset 102*a* (or a new subset) is different than that originally applied. For instance, the annotator can adjust the clinical concepts and/or categories that control the additional multimodal data (e.g., in addition to the GT annotation data). For example, continuing with the lesion segmentation example, the expert annotator may determine that the performance of the model may be improved with additional description text describing the relative location of the observed lesion in the image, or a description of the size of the lesion, and so on. Thus, at 118 the expert annotator can update or adjust the multimodal annotation criteria defined at 104 accordingly. At 106, the expert annotator can further update the text annotation data applied to the subset 102*a* and generate updated multimodal annotation data for the subset 102*a* (and/or a new subset) in accordance with the updated criteria. At 108, the (updated) annotated subset 102*a*' can then be used to retrain or update the one or more AI models. To this end, the machine learning system can employ the one or more machine learning processes to learn updated mappings between the updated non-image (e.g., text data) annotation data and the image features and generate updated versions of the models 110 based on the updated mappings. Process 100 can further continue in accordance with steps 112 and 114 as described above using the updated version of the models. Process 100 can further be iteratively performed in accordance with the dashed arrow line flow until the performance of the model is acceptable at 116. In this regard, with the disclosed techniques, the expert annotator can control and provide the annotation data that controls the performance of the model prior to deployment of the model in runtime environments.

Figure 4:
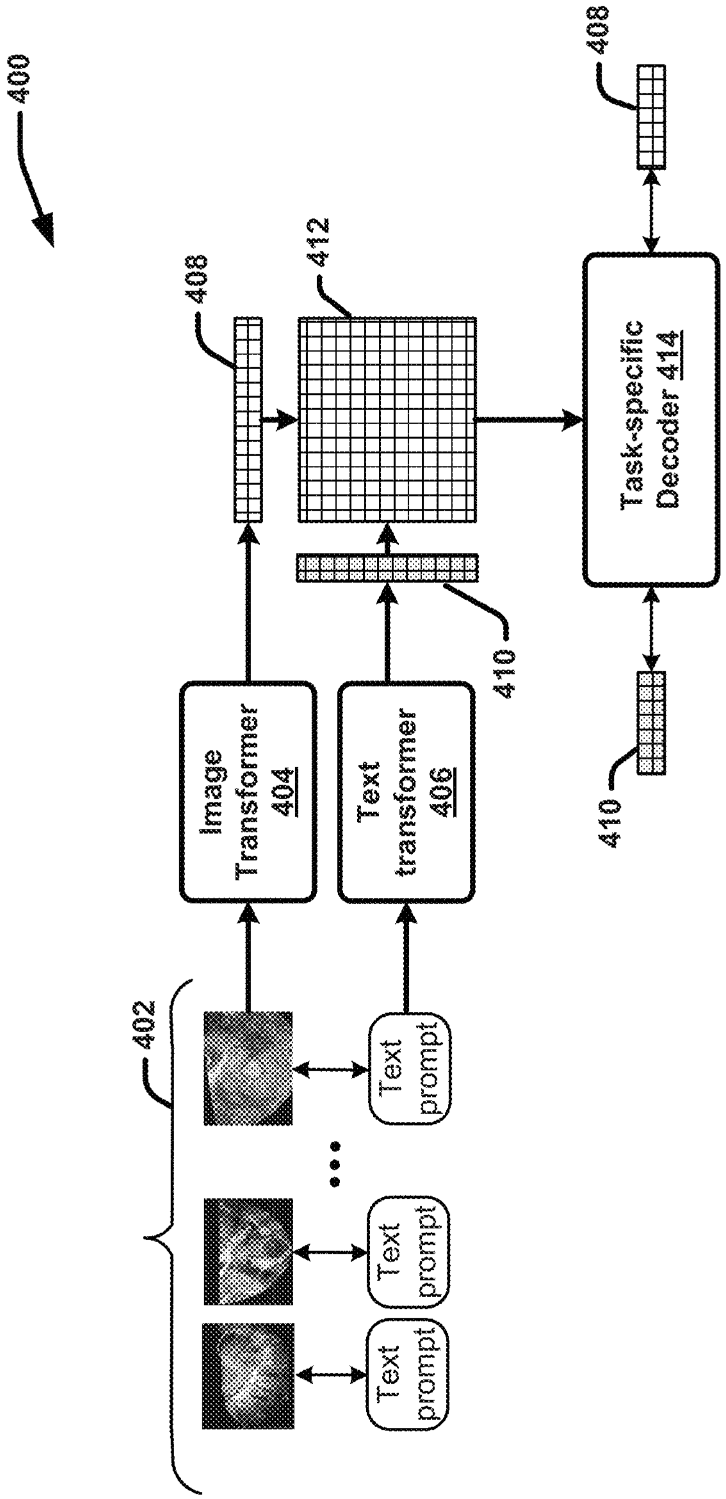
FIG. 4 presents an example training process for generating one or more multimodal AI models tailored to specific concepts in medical imaging, in accordance with one or more embodiments of the disclosed subject matter.

FIG. 4 presents an example training process 400 for generating one or more multimodal AI models tailored to specific concepts in medical imaging, in accordance with one or more embodiments of the disclosed subject matter. With reference to FIGS. 1-4, in various embodiments, training process 400 can be employed to build one or more of the multimodal models 110 described with reference to step 108 of process 100. In accordance with process 400, the multimodal model includes three components or sub-models, including an image transformer 404, a text transformer 406, and a task-specific decoder 414. The image transformer 404, the text transformer 406 and the task-specific decoder 414 can respectively correspond to deep learning neural network models. In this example, the multimodal model is being trained to process multimodal input data 402 consisting of medical images paired with text prompt data. The text prompt data can correspond to annotator provided text describing relevant features of the medical images, such as relevant features of the medical images for a target task, such as lesion segmentation for instance. In some embodiments, the medical images can include mark-up annotation data applied thereto (e.g., bounding boxes, masks, etc.) that mark relevant anatomical features of interest described in the text prompts (e.g., descriptions of mark-up lesions).

In various embodiments, the image transformer 404 can transform each input medical image into an image vector representation 408 of that image. At the same time, the text transformer 406 can transform the corresponding text prompt into a text representation vector 410 of the text prompt using natural language processing (NLP) processing techniques. The image transformer 404 and the text transformer 406 can further be configured to project the respective vectors representations onto a common dimensional space 412. The task-specific decoder 414 can further learn mappings between the text prompt features as represented in the text representation vector 410 and the image features as represented in the image representation vector 408 using one or more unsupervised machine learning processes. In various embodiments, as a result of learning these mappings for all of the training samples 402 (i.e., included in the subset 102*a*), the task-specific decoder 414 can further be trained to perform one or more bi-directional inferencing tasks for the medical images. For example, the task-specific decoder 414 can be trained to detect and generate segmentation data (e.g., bounding box data, a mask, etc.) for a target anatomical feature (e.g., a lesion for instance) give the input medical image and a corresponding text prompt describing the target anatomical feature.

Figure 5:
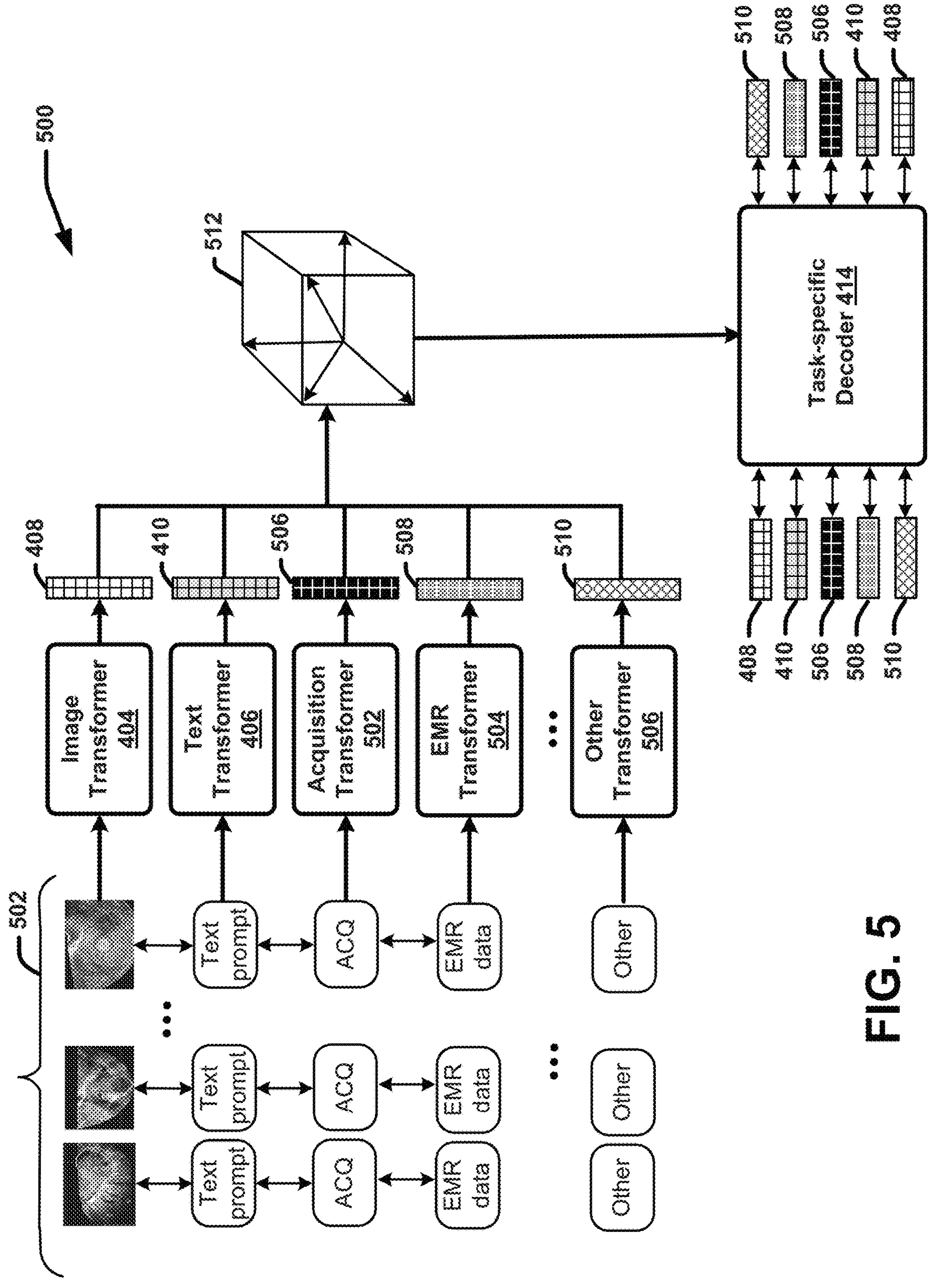
FIG. 5 presents another example training process for generating one or more multimodal AI models tailored to specific concepts in medical imaging, in accordance with one or more embodiments of the disclosed subject matter.

FIG. 5 presents another example training process 500 for generating one or more multimodal AI models tailored to specific concepts in medical imaging, in accordance with one or more embodiments of the disclosed subject matter. With reference to FIGS. 1-5, training process 500 is similar to training process 400 with the addition of additional multimodal input data associated with the medical images. Repetitive description of like elements employed in respective embodiments is omitted for sake of brevity.

In various embodiments, training process 500 can be employed to build one or more of the multimodal models 110 described with reference to step 108 of process 100. In accordance with process 500, the multimodal model includes the three components or sub-models described with reference to process 400. In addition, the multimodal model can include additional transformers, one for each of the additional forms of multimodal input (e.g., acquisition transformer 502, EMR transformer 504, and/or one or more other transformers 506).

As described above, text prompt data corresponding to unstructured text input provided by the expert annotator can correspond to one form of multimodal data that can be paired with the respective medical images. Various other forms of multimodal data can also be paired with the input images, including acquisition (ACQ) parameter data that describes acquisition parameters (e.g., metadata) of the medical images, EMR data providing various relevant information about the patient and the medical images, and various other forms of clinical and non-clinical data. With these embodiments, the multimodal model is being trained to process multimodal input data 502 consisting of medical images paired with text prompt data, acquisition data, EMR data and potentially various other forms. To this end, the multimodal model can include sperate transformers for each of the different types of multimodal input data. Each of the transformers (e.g., the image transformer 404, the text transformers 406, the acquisition transformer 504, and/or one or more other transformers 506 can respectively generate representation vectors of the corresponding input data types (e.g., image representation vector 408, text representation vector 410, ACQ representation vector 506, EMR representation vector 508, and/or other representation vectors 510). The respective transformers can further be configured to project the respective vectors representations onto a common multi-dimensional space 512.

The task-specific decoder 414 can further learn mappings between the different image and non-image features associated with the different multimodal inputs based on their projected vector representations and one or more unsupervised machine learning processes. In various embodiments, as a result of learning these mappings for the training samples 502 (i.e., included in the subset 102*a*), the task-specific decoder 414 can further be trained to perform one or more bi-directional inferencing tasks for the medical images. For example, the task-specific decoder 414 can be trained to detect and generate segmentation data (e.g., bounding box data, a mask, etc.) for a target anatomical feature (e.g., a lesion for instance) given the input medical image and one or more additional forms of input (e.g., text prompt data, acquisition data, EMR data, etc.).

Figure 6:
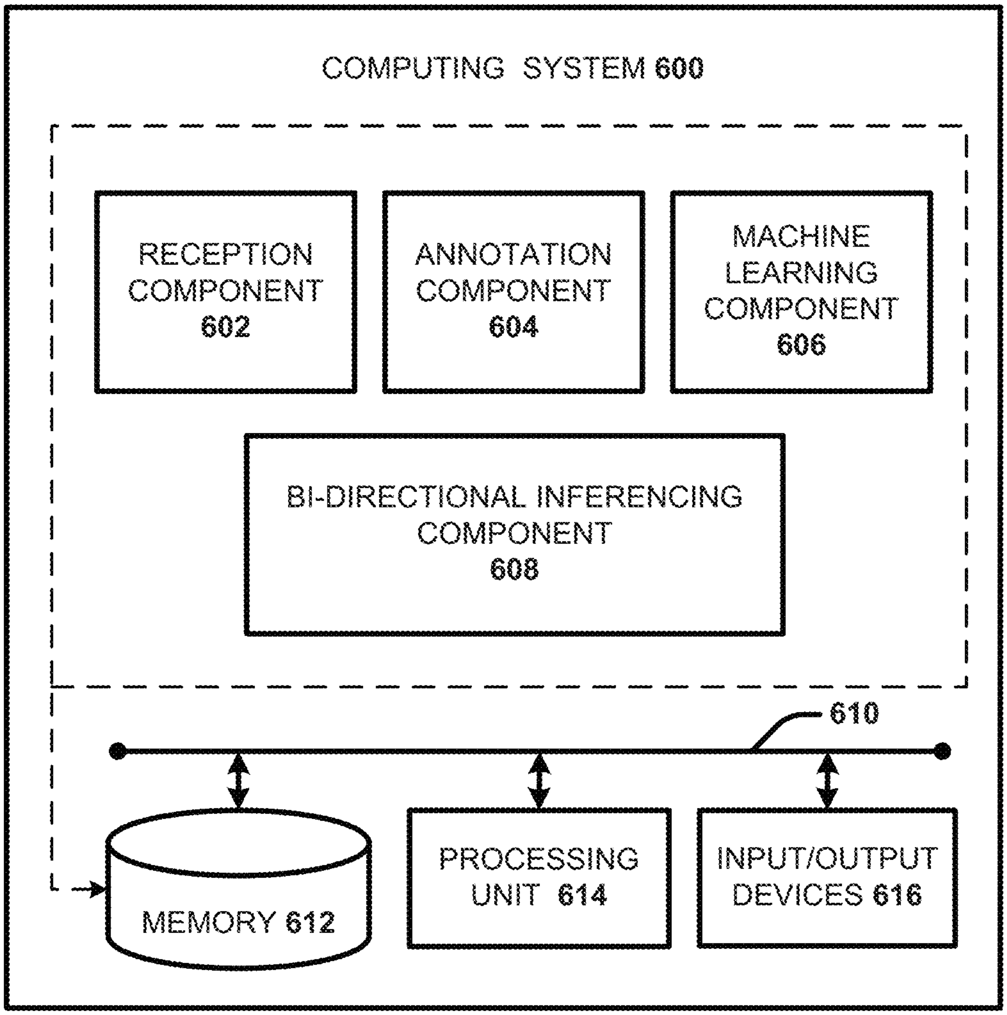
FIG. 6 illustrates a block diagram of an example, non-limiting computer system that facilitates an iterative framework for learning multimodal mappings tailored to medical image inferencing tasks, in accordance with one or more embodiments of the disclosed subject matter.

FIG. 6 illustrates a block diagram of an example, non-limiting computer system 600 that facilitates an iterative framework for learning multimodal mappings tailored to medical image inferencing tasks, in accordance with one or more embodiments of the disclosed subject matter. With reference to FIGS. 1-6, computing system 600 can include or correspond to one or more one or more computing systems that can perform or facilitate performance of the operations described with reference to process 100 and other processes described herein (e.g., process 400, process 500, and the like). In this regard, system 600 can include or correspond to one or more computing devices, machines, virtual machines, computer-executable components, datastores, and the like that may communicatively coupled to one another either directly or via one or more wired or wireless communication frameworks.

Computing system 600 can include machine-executable (i.e., computer-executable) components or instructions embodied within one or more machines (e.g., embodied in one or more computer-readable storage media associated with one or more machines) that can perform one or more of the operations described with reference to process 100 and additional processes described herein. For example, computing system 600 can include (or be operatively coupled to) at least one memory 612 that stores computer-executable components and at least one processor (e.g., processing unit 614) that executes the computer-executable components stored in the at least one memory 612. These computer-executable components can include (but are not limited to) reception component 602, annotation component 604, machine learning component 606, and bi-directional inferencing component 608. In some embodiments, the memory 612 some or all of the data (e.g., the medical image dataset, the multimodal annotation data, the model output data, etc.) and/or models 110 (e.g., including pre-trained versions, partially trained versions, intermediate versions, and finalized versions) described with reference to FIGS. 1-5. Examples of said and memory and processor as well as other suitable computer or computing-based elements, can be found with reference to FIG. 9 (e.g., processing unit 904 and system memory 906 respectively), and can be used in connection with implementing one or more of the systems or components shown and described in connection with FIG. 6, or other figures disclosed herein.

The computing system 600 can further include one or more input/output devices 616 to facilitate receiving user input and rendering data to users in association with performing various operations described with respect to the machine-executable components and/or process 100 and additional processes described herein. Suitable examples of the input/output devices 616 are described with reference to FIG. 9 (e.g., input devices 928 and output device 936). The computing system 100 can further include a system bus 610 that couples the memory 612, the processing unit 614 and the input/output device 616 to one another.

With reference to FIGS. 1 and 6, in one or more embodiments, the reception component 602 can receive the multimodal annotation data for the medical images included a medical image dataset 102. For example, the reception component 602 can receive the annotated subset 102*a*' in response to generation thereof by the expert annotator. In some embodiments, the annotation component 604 can include or correspond to a medical imaging application that allows the annotator to view the medical images included in the subset 102*a* as displayed via GUI (and a display device), apply mark-up annotation data to the medical images (e.g., using existing medical image mark-up annotation software), provide unstructured texts input describing relevant image features (e.g., via free form data entry, via speech which is then converted to text, of via another suitable input mechanism), and optionally generate and/or provide (e.g., import, upload, provide links to, etc.) additional input in the form of relevant medical records, laboratory reports, metadata, related medical images, and the like. With these embodiments, the reception component 602 can receive the annotated subset 102*a* in response to generation thereof by the expert annotator using the annotation component 604. In some embodiments, the annotation component 604 can also facilitate receiving input from the expert annotator defining the multimodal annotation criteria (in accordance with stop 104 of process 100). With these embodiments, in association with receiving the annotated subset 102*a*, the reception component can also receive the multimodal annotation criteria applied by the annotator.

The machine learning component 606 can perform the multimodal model building (or training) operations described with reference to step 108 of process 100. To this end, the machine learning component 606 can train and generate one or more multimodal AI models 110 using the annotated subset 102*a*' and one or more machine learning processes. For example, in some embodiments, the machine learning component 606 can perform the training process 400 and 500 described with reference to FIGS. 4 and 5 to generate various bi-directional models capable of relating medical images and/or image features included in the medical images to corresponding non-image features (e.g., text features, acquisition parameter features, patient EMR features, etc.). In this regard, the machine learning component 606 can employs one or more machine learning processes to learn bi-directional mappings between non-image features included in the non-image annotation data applied to the medical images (e.g., text data and/or other forms of forms of multimodal annotation data, excluding the medical images themselves), and image features associated with the medical images. In embodiments in which the multimodal annotation data include image annotation data, such as mark-up data applied to the medical images (e.g., bounding boxes, masks, etc.) in association with learning the bi-directional mappings, the machine learning component 606 can use such GT image annotation data to facilitate learning bi-directional mappings with marked image features. In this regard, the machine learning component 606 can employ one or more machine learning processes to learn bi-directional mappings between non-image features included in the non-image annotation data applied to the medical images, and image features associated with the medical images and the image annotation data (e.g., the mark-up data).

As a result of the one or more machine learning processes, the machine learning component 606 can further generate one or more models (e.g., models 110) configured to infer one or more of the non-image features associated with new medical images (e.g., included in the additional medical images 102*b* or corresponding runtime environment medical images) given the new medical images. Additionally, or alternatively as a result of the one or more machine learning processes, the machine learning component 606 can generate one or more models (e.g., model 110) configured to infer one or more of the image features associated with the new medical images given the new medical images and non-image input identifying or indicating one or more of the non-image features respectively associated with the new medical images.

In various embodiments, the bi-directional inferencing component 608 can execute one or more of the trained versions of the models on new medical images corresponding to the training images in association with the iterative annotation and model building process (e.g., the dashed arrow line flow of process 100). Additionally, or alternatively, the bi-directional inferencing component 608 can execute one or more of the trained versions and finalized version of the models 110 on new medical images corresponding to the training images in runtime environments. For example, the bi-directional inferencing component 608 can execute a model tuned to perform a querying task to facilitate finding relevant medical images that satisfy a text prompt query. In another example, the bi-directional inferencing component 608 can execute one or more of the models 110 in association with performing smart medical reporting.

Additionally, or alternatively, as applied to a model tuned to perform smart annotation on medical images corresponding to the training images, the annotation component 604 can be configured to execute the smart annotation model in association with receiving corresponding text prompts from the expert annotator (e.g., in accordance with step 112). With these embodiments, the annotation component 604 can also provide for reviewing results of the smart annotation model and updating the multimodal criteria, in accordance with steps 114, 116 and 118 of process 100.

FIG. 7 illustrates a block diagram of an example, non-limiting computer implemented method 700 for generating one or more multimodal AI models tailored to specific concepts in medical imaging, in accordance with one or more embodiments of the disclosed subject matter. At 702, method 700 can comprise, receiving, by a system comprising a processor (e.g., computing system 600), multimodal annotation data for medical images included a medical image dataset, the multimodal annotation data comprising non-image annotation data (e.g., natural language text data provided by the expert annotator, EMR data, acquisition parameter data, laboratory data, etc.) and image annotation data (e.g., mark-up data marking and/or defining one or more anatomical features, artifacts, regions of interest, etc.). At 704, method 700 further comprises employing, by the system, one or more machine learning processes to learn bi-directional mappings between non-image features included in the non-image annotation data and image features associated with the medical images and the image annotation data (e.g., via the machine learning component 606). At 706, method 700 further comprises generating, by the system as a result of the one or more machine learning processes (e.g., via the machine learning component 606), a model (e.g., of models 110) configured to infer one or more of the non-image features associated with new medical (e.g., the additional medical images 102*b* and/or corresponding runtime environment medical images) images given the new medical images. For example, in various embodiments, the one or more machine learning processes can involve employing/training one or more transformer models and/or one or more task-specific decoder models (e.g., a CLIP model, a CLIP-SEG model or the like) to learn the bi-directional mappings using the annotated subset 102*a*', and training a task-specific decoder 414 in association with training the one or more transformer models and/or one or more task-specific decoder models to perform a specific bi-directional inferencing task on the medical images using the learned mappings.

FIG. 8 illustrates a block diagram of another example, non-limiting computer implemented method 800 for generating one or more multimodal AI models tailored to specific concepts in medical imaging, in accordance with one or more embodiments of the disclosed subject matter. At 802, method 800 can comprise, receiving, by a system comprising a processor (e.g., computing system 600), multimodal annotation data for medical images included a medical image dataset, the multimodal annotation data comprising non-image annotation data (e.g., natural language text data provided by the expert annotator, EMR data, acquisition parameter data, laboratory data, etc.) and image annotation data (e.g., mark-up data marking and/or defining one or more anatomical features, artifacts, regions of interest, etc.). At 804, method 800 further comprises employing, by the system, one or more machine learning processes to learn bi-directional mappings between non-image features included in the non-image annotation data and image features associated with the medical images and the image annotation data (e.g., via the machine learning component 606). At 806, method 800 further comprises generating, by the system as a result of the one or more machine learning processes (e.g., via the machine learning component 606), a model (e.g., of models 110) model configured to infer one or more of the image features associated with new medical images (e.g., additional medical images 102*b*' and/or runtime environment medical images) given the new medical images and non-image input (e.g., unstructured text prompt data) identifying or indicating one or more of the non-image features respectively associated with the new medical images. For example, in various embodiments, the one or more machine learning processes can involve employing/training one or more transformer models and/or one or more task-specific decoder models (e.g., a CLIP model, a CLIP-SEG model or the like) to learn the bi-directional mappings using the annotated subset 102*a*', and training a task-specific decoder 414 in association with training the one or more transformer models and/or one or more task-specific decoder models to generate segmentation annotation data corresponding to the image annotation data (e.g., bounding box data, mask data, or the like) for the new medical images defining one or more target anatomical features of interest.

EXAMPLE OPERATING ENVIRONMENTS

One or more embodiments can be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. To this end, the a computer readable storage medium, a machine-readable storage medium, or the like as used herein can include a non-transitory computer readable storage medium, a non-transitory machine-readable storage medium, and the like.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 9, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 9:
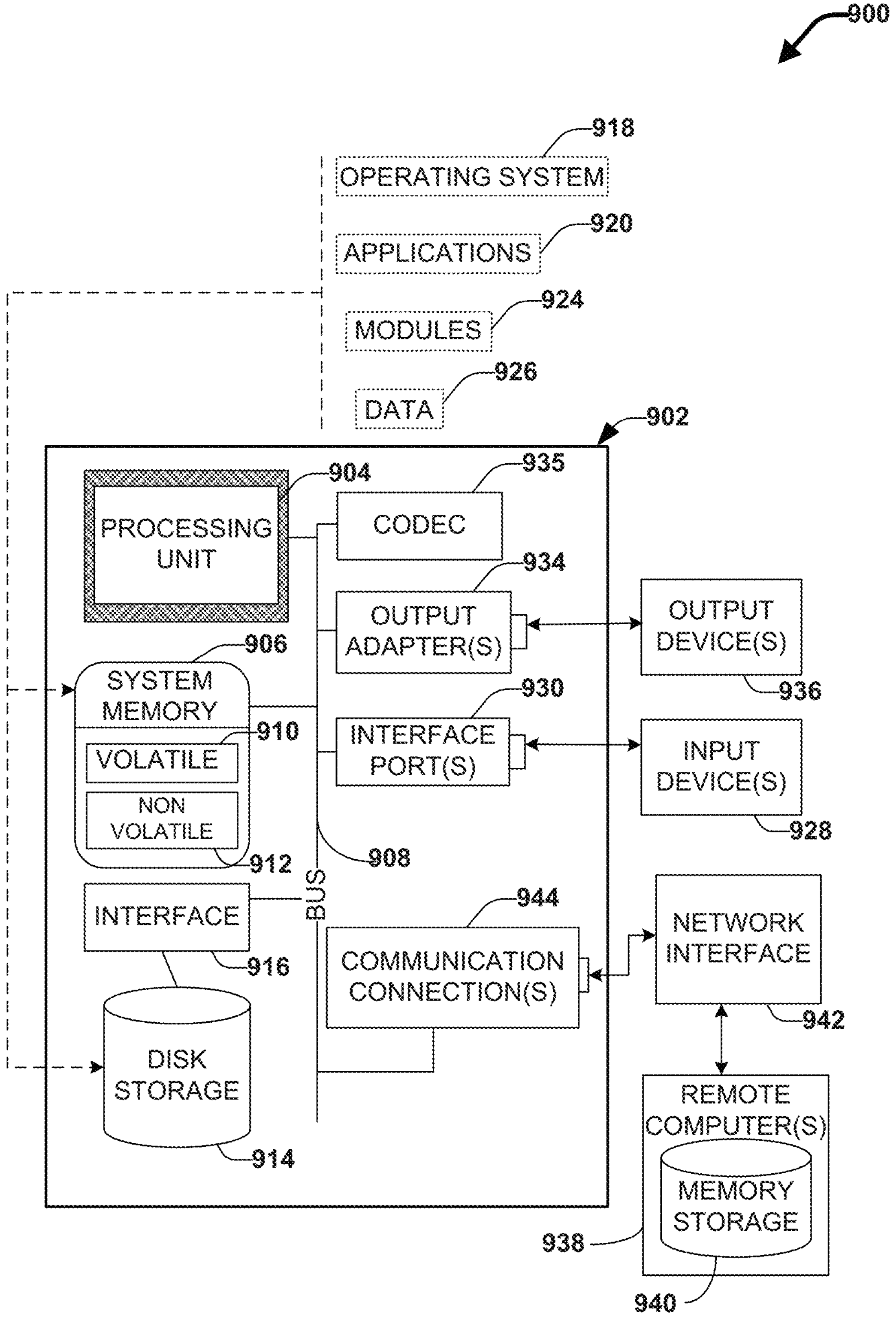
FIG. 9 illustrates a block diagram of an example, non-limiting operating environment in which one or more embodiments described herein can be facilitated.

With reference to FIG. 9, an example environment 900 for implementing various aspects of the claimed subject matter includes a computer 902. The computer 902 includes a processing unit 904, a system memory 906, a codec 935, and a system bus 908. The system bus 908 couples system components including, but not limited to, the system memory 906 to the processing unit 904. The processing unit 904 can be any of various available processors. Dual microprocessors and other multiprocessor architectures also can be employed as the processing unit 904.

The system bus 908 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 906 includes volatile memory 910 and non-volatile memory 912, which can employ one or more of the disclosed memory architectures, in various embodiments. The basic input/output system (BIOS), containing the basic routines to transfer information between elements within the computer 902, such as during start-up, is stored in non-volatile memory 912. In addition, according to present innovations, codec 935 can include at least one of an encoder or decoder, wherein the at least one of an encoder or decoder can consist of hardware, software, or a combination of hardware and software. Although, codec 935 is depicted as a separate component, codec 935 can be contained within non-volatile memory 912. By way of illustration, and not limitation, non-volatile memory 912 can include read only memory (ROM), programmable ROM (PROM), electrically programmable ROM (EPROM), electrically crasable programmable ROM (EEPROM), Flash memory, 3D Flash memory, or resistive memory such as resistive random access memory (RRAM). Non-volatile memory 912 can employ one or more of the disclosed memory devices, in at least some embodiments. Moreover, non-volatile memory 912 can be computer memory (e.g., physically integrated with computer 902 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 910 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 902 can also include removable/non-removable, volatile/non-volatile computer storage medium. FIG. 9 illustrates, for example, disk storage 914. Disk storage 914 includes, but is not limited to, devices like a magnetic disk drive, solid state disk (SSD), flash memory card, or memory stick. In addition, disk storage 914 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 914 to the system bus 908, a removable or non-removable interface is typically used, such as interface 916. It is appreciated that disk storage 914 can store information related to a user. Such information might be stored at or provided to a server or to an application running on a user device. In one embodiment, the user can be notified (e.g., by way of output device(s) 936) of the types of information that are stored to disk storage 914 or transmitted to the server or application. The user can be provided the opportunity to opt-in or opt-out of having such information collected or shared with the server or application (e.g., by way of input from input device(s) 928).

It is to be appreciated that FIG. 9 describes software that acts as an intermediary between users and the basic computer resources described in the suitable operating environment 900. Such software includes an operating system 910. Operating system 910, which can be stored on disk storage 914, acts to control and allocate resources of the computer 902. Applications 920 take advantage of the management of resources by operating system 910 through program modules 924, and program data 926, such as the boot/shutdown transaction table and the like, stored either in system memory 906 or on disk storage 914. It is to be appreciated that the claimed subject matter can be implemented with various operating systems or combinations of operating systems.

A user enters commands or information into the computer 902 through input device(s) 928. Input devices 928 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 904 through the system bus 908 via interface port(s) 930. Interface port(s) 930 include, for example, a serial port, a parallel port, a game port, and a universal serial bus (USB). Output device(s) 936 use some of the same type of ports as input device(s) 928. Thus, for example, a USB port can be used to provide input to computer 902 and to output information from computer 902 to an output device 936. Output adapter 934 is provided to illustrate that there are some output devices 936 like monitors, speakers, and printers, among other output devices 936, which require special adapters. The output adapters 934 include, by way of illustration and not limitation, video and sound cards that provide a means of connection between the output device 936 and the system bus 908. It should be noted that other devices or systems of devices provide both input and output capabilities such as remote computer(s) 938.

Computer 902 can operate in a networked environment using logical connections to one or more remote computers, such as remote computer(s) 938. The remote computer(s) 938 can be a personal computer, a server, a router, a network PC, a workstation, a microprocessor based appliance, a peer device, a smart phone, a tablet, or other network node, and typically includes many of the elements described relative to computer 902. For purposes of brevity, only a memory storage device 940 is illustrated with remote computer(s) 938. Remote computer(s) 938 is logically connected to computer 902 through a network interface 942 and then connected via communication connection(s) 944. Network interface 942 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 944 refers to the hardware/software employed to connect the network interface 942 to the bus 908. While communication connection 944 is shown for illustrative clarity inside computer 902, it can also be external to computer 902. The hardware/software necessary for connection to the network interface 942 includes, for exemplary purposes only, internal and external technologies such as, modems including regular telephone grade modems, cable modems and DSL modems, ISDN adapters, and wired and wireless Ethernet cards, hubs, and routers.

Figure 10:
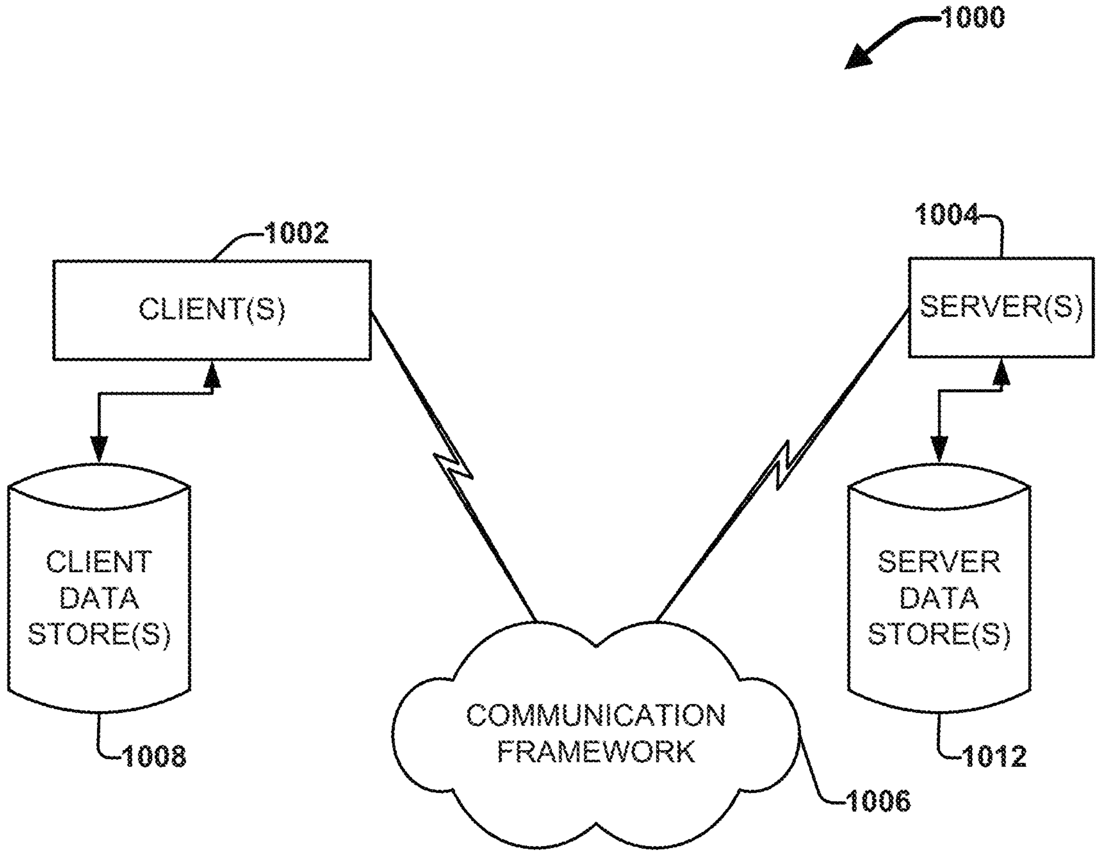
FIG. 10 illustrates a block diagram of another example, non-limiting operating environment in which one or more embodiments described herein can be facilitated.

FIG. 10 is a schematic block diagram of a sample-computing environment 1000 with which the subject matter of this disclosure can interact. The system 1000 includes one or more client(s) 1002. The client(s) 1002 (e.g., corresponding to client system 700 in some embodiments) can be hardware and/or software (e.g., threads, processes, computing devices). The system 1000 also includes one or more server(s) 1004 (e.g., corresponding to computing system 600 in some embodiments). Thus, system 1000 can correspond to a two-tier client server model or a multi-tier model (e.g., client, middle tier server, data server), amongst other models. The server(s) 1004 can also be hardware and/or software (e.g., threads, processes, computing devices). The servers 1004 can house threads to perform transformations by employing this disclosure, for example. One possible communication between a client 1002 and a server 1004 may be in the form of a data packet transmitted between two or more computer processes (e.g., comprising feedback information 132 for instance).

The system 1000 includes a communication framework 1006 that can be employed to facilitate communications between the client(s) 1002 and the server(s) 1004. The client(s) 1002 are operatively connected to one or more client data store(s) 1008 that can be employed to store information local to the client(s) 1002. Similarly, the server(s) 1004 are operatively connected to one or more server data store(s) 1012 that can be employed to store information local to the servers 1004.

It is to be noted that aspects or features of this disclosure can be exploited in substantially any wireless telecommunication or radio technology, e.g., Wi-Fi; Bluetooth; Worldwide Interoperability for Microwave Access (WiMAX); Enhanced General Packet Radio Service (Enhanced GPRS); Third Generation Partnership Project (3GPP) Long Term Evolution (LTE); Third Generation Partnership Project 2 (3GPP2) Ultra Mobile Broadband (UMB); 3GPP Universal Mobile Telecommunication System (UMTS); High Speed Packet Access (HSPA); High Speed Downlink Packet Access (HSDPA); High Speed Uplink Packet Access (HSUPA); GSM (Global System for Mobile Communications) EDGE (Enhanced Data Rates for GSM Evolution) Radio Access Network (GERAN); UMTS Terrestrial Radio Access Network (UTRAN); LTE Advanced (LTE-A); etc. Additionally, some or all of the aspects described herein can be exploited in legacy telecommunication technologies, e.g., GSM. In addition, mobile as well non-mobile networks (e.g., the Internet, data service network such as internet protocol television (IPTV), etc.) can exploit aspects or features described herein.

While the subject matter has been described above in the general context of computer-executable instructions of a computer program that runs on a computer and/or computers, those skilled in the art will recognize that this disclosure also can or may be implemented in combination with other program modules. Generally, program modules include routines, programs, components, data structures, etc. that perform particular tasks and/or implement particular abstract data types. Moreover, those skilled in the art will appreciate that the inventive methods may be practiced with other computer system configurations, including single-processor or multiprocessor computer systems, mini-computing devices, mainframe computers, as well as personal computers, hand-held computing devices (e.g., PDA, phone), microprocessor-based or programmable consumer or industrial electronics, and the like. The illustrated aspects may also be practiced in distributed computing environments where tasks are performed by remote processing devices that are linked through a communications network. However, some, if not all aspects of this disclosure can be practiced on stand-alone computers. In a distributed computing environment, program modules may be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

In another example, respective components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

Various aspects or features described herein can be implemented as a method, apparatus, system, or article of manufacture using standard programming or engineering techniques. In addition, various aspects or features disclosed in this disclosure can be realized through program modules that implement at least one or more of the methods disclosed herein, the program modules being stored in a memory and executed by at least a processor. Other combinations of hardware and software or hardware and firmware can enable or implement aspects described herein, including a disclosed method(s). The term "article of manufacture" as used herein can encompass a computer program accessible from any computer-readable device, carrier, or storage media. For example, computer readable storage media can include but are not limited to magnetic storage devices (e.g., hard disk, floppy disk, magnetic strips . . . ), optical discs (e.g., compact disc (CD), digital versatile disc (DVD), blu-ray disc (BD) . . . ), smart cards, and flash memory devices (e.g., card, stick, key drive . . . ), or the like.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor may also be implemented as a combination of computing processing units.

In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory.

By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or methods herein are intended to include, without being limited to including, these and any other suitable types of memory.

It is to be appreciated and understood that components, as described with regard to a particular system or method, can include the same or similar functionality as respective components (e.g., respectively named components or similarly named components) as described with regard to other systems or methods disclosed herein.

What has been described above includes examples of systems and methods that provide advantages of this disclosure. It is, of course, not possible to describe every conceivable combination of components or methods for purposes of describing this disclosure, but one of ordinary skill in the art may recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

What is claimed is:

1. A system, comprising:

a memory that stores computer-executable components; and a processor that executes the computer-executable components stored in the memory, wherein the computer-executable components comprise:

a reception component that receives multimodal annotation data for medical images included a medical image dataset, the multimodal annotation data comprising non-image annotation data and image annotation data;

a machine learning component that employs one or more machine learning processes to train a model to learn bi-directional mappings between non-image features included in the non-image annotation data and image features associated with the medical images and the image annotation data, wherein the non-image annotation data and the bi-directional mappings are tailored based on a target medical image inferencing task and a type of the medical images; and an inference component that employs the model to infer one or more of the image features associated with new medical images given the new medical images and non-image input identifying or indicating one or more of the non-image features respectively associated with the new medical images.

2. The system of claim 1, wherein as a result of the one or more machine learning processes, the machine learning component configures the model to infer one or more of the non-image features associated with the new medical images given the new medical images.

3. The system of claim 2, wherein the non-image annotation data adheres to one or more criteria, wherein the reception component receives updated non-image annotation data for the medical images that adheres to one or more updated criteria based on one or more errors associated with performance of the model on the new medical images, wherein the machine learning component employs one or more second machine learning processes to train the model to learn updated bi-directional mappings between updated non-image features included in the updated non-image annotation data and the image features associated with the medical images and the image annotation data, and wherein as a result of the one or more second machine learning processes, the machine learning component generates an updated version of the model configured to more accurately infer the one or more of the non-image features associated with the new medical images given the new medical images.

4. The system of claim 1, wherein the non-image annotation data adheres to one or more criteria, wherein the reception component receives updated non-image annotation data for the medical images that adheres to one or more updated criteria based on one or more errors associated with performance of the model on the new medical images, wherein the machine learning component employs one or more second machine learning processes to retrain the model to learn updated bi-directional mappings between updated non-image features included in the updated non-image annotation data and the image features associated with the medical images and the non-image annotation data, and wherein as a result of the one or more second machine learning processes, the machine learning component generates an updated version of the model configured to more accurately infer the one or more of the image features associated with new medical images given the new medical images and the non-image input.

5. The system of claim 1, wherein in association with inferring the one or more of the image features, the machine learning component configures the model to generate new image annotation data for the new medical images defining the one or more of the image features.

6. The system of claim 5, wherein the image annotation data and the new image annotation data comprises mark-up data applied to the medical images marking one or more anatomical features and the non-image annotation data and the non-image input respectively comprise text data.

7. The system of claim 5, wherein the computer-executable components further comprise:

an annotation component that employs the model to generate the new image annotation data for the new medical images given the new medical images and the non-image input, wherein the new medical images are included in the medical image dataset.

8. The system of claim 1, wherein the non-image annotation data adheres to defined clinical criteria.

9. The system of claim 1, wherein the non-image annotation data comprises unstructured text data.

10. The system of claim 9, wherein the unstructured text data comprises natural language text data describing clinical interpretations of the medical images.

11. The system of claim 10, wherein the reception component receives the natural language text data from a single entity and wherein the bi-directional mappings are tailored to a natural language employed by the single entity.

12. The system of claim 1, wherein the non-image annotation data comprises patient information regarding respective patients represented in the medical images as included in one or more electronic medical record data files.

13. A method, comprising:

receiving, by a system comprising a processor, multimodal annotation data for medical images comprising a medical image dataset, the multimodal annotation data comprising non-image annotation data and image annotation data;

employing, by the system, one or more machine learning processes to train a model to learn bi-directional mappings between non-image features included in the non-image annotation data and image features associated with the medical images and the image annotation data, wherein the non-image annotation data and the bi-directional mappings are tailored based on a target medical image inferencing task and a type of the medical images; and employing, by the system, the model to infer one or more of the image features associated with new medical images given the new medical images and non-image input identifying or indicating one or more of the non-image features respectively associated with the new medical images.

14. The method of claim 13, further comprising:

employing, by the system, the model to infer one or more of the non-image features associated with the new medical images given the new medical images.

15. The method of claim 13, further comprising:

configuring, by the system, the model to generate new image annotation data for the medical images defining the one or more of the image features; and employing, by the system, the model to generate the new image annotation data for the new medical images given the new medical images and the non-image input, wherein the new medical images are included in the medical image dataset.

16. The method of claim 15, wherein the image annotation data and the new image annotation data comprises mark-up data respectively applied to the medical images and the new medical images marking one or more anatomical features and the non-image annotation data and the non-image input respectively comprise text data.

17. The method of claim 13, wherein the non-image annotation data comprises natural language text data describing clinical interpretations of the medical images in accordance with one or more defined criteria.

18. A non-transitory machine-readable storage medium, comprising executable instructions that, when executed by a processor, facilitate performance of operations, comprising:

receiving receives multimodal annotation data for medical images included a medical image dataset, the multimodal annotation data comprising non-image annotation data and image annotation data;

employing one or more machine learning processes to learn bi-directional mappings between non-image features included in the non-image annotation data and image features associated with the medical images and the image annotation data wherein the non-image annotation data and the bi-directional mappings are tailored based on a target medical image inferencing task and a type of the medical images; and generating, as a result of the one or more machine learning processes, a model configured to:

infer one or more of the non-image features associated with new medical images given the new medical images, and infer one or more of the image features associated with the new medical images given the new medical images and non-image input identifying or indicating one or more of the non-image features respectively associated with the new medical images; and employing the model to infer the one or more non-image features or the one or more image features associated with the new medical images.

19. The non-transitory machine-readable storage medium of claim 18, wherein the generating further comprises configuring the model to generate new image annotation data for the new medical images defining the one or more of the image features, and wherein the employing comprises employing the model to generate the new image annotation data.

20. The non-transitory machine-readable storage medium of claim 19, wherein the image annotation data and the new image annotation data comprises mark-up data respectively applied to the medical images and the new medical images marking one or more anatomical features and the non-image annotation data and the non-image input respectively comprise text data.

* * * * *